US009802324B2

(12) United States Patent
Iida

(10) Patent No.: US 9,802,324 B2
(45) Date of Patent: Oct. 31, 2017

(54) POSITION DETECTION SENSOR AND MANIPULATOR

(71) Applicant: OLYMPUS CORPORATION, Tokyo (JP)

(72) Inventor: Masatoshi Iida, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 230 days.

(21) Appl. No.: 14/740,465

(22) Filed: Jun. 16, 2015

(65) Prior Publication Data

US 2016/0001447 A1    Jan. 7, 2016

Related U.S. Application Data

(63) Continuation of application No. PCT/JP2013/084394, filed on Dec. 17, 2013.

(Continued)

(51) Int. Cl.
*B25J 13/08* (2006.01)
*A61B 34/20* (2016.01)
(Continued)

(52) U.S. Cl.
CPC ............ *B25J 13/088* (2013.01); *A61B 34/20* (2016.02); *A61B 34/30* (2016.02); *A61B 34/35* (2016.02);
(Continued)

(58) Field of Classification Search
CPC ........... A61B 2017/00526; A61B 2017/00929; A61B 2034/2059; A61B 2034/2061; A61B 34/20
(Continued)

(56) References Cited

U.S. PATENT DOCUMENTS 2,773,995 A   12/1956   Griswold
5,572,119 A * 11/1996   Taylor ................. F16C 32/0446
                                                    174/261
(Continued)

FOREIGN PATENT DOCUMENTS

JP   S59-040603 U   3/1984
JP   S61-152121 U   9/1986
(Continued)

OTHER PUBLICATIONS

Extended Supplementary European Search Report dated Aug. 24, 2016 received in Application No. 13863726.9.
(Continued)

*Primary Examiner* — Yaritza Guadalupe-McCall
(74) *Attorney, Agent, or Firm* — Scully, Scott, Murphy & Presser, P.C.

(57) ABSTRACT

A position detection sensor includes: a linear member; a conductive portion and an insulating portion provided in an outer periphery of the linear member and arranged side by side in a direction of an axis of the linear member; a support member having insulating properties and provided so as to be capable of being relatively advanced or retracted in the direction of the axis with respect to the conductive portion and the insulating portion; and a conductive contact member attached to the support member and configured such that a distal end of the contact member comes in contact with outer surfaces of the conductive portion and the insulating portion by a biasing force toward the outer surfaces of the conductive portion and the insulating portion.

18 Claims, 26 Drawing Sheets

Related U.S. Application Data

(60) Provisional application No. 61/740,010, filed on Dec. 20, 2012, provisional application No. 61/766,214, filed on Feb. 19, 2013.

(51) Int. Cl.

| | | |
|---|---|---|
| *A61B 34/30* | (2016.01) | |
| *A61B 34/37* | (2016.01) | |
| *A61B 34/35* | (2016.01) | |
| *G01D 5/245* | (2006.01) | |
| *G01D 5/165* | (2006.01) | |
| *A61B 17/00* | (2006.01) | |

(52) U.S. Cl.
CPC .............. *A61B 34/37* (2016.02); *G01D 5/165* (2013.01); *G01D 5/2451* (2013.01); *A61B 2017/00526* (2013.01); *A61B 2017/00929* (2013.01); *A61B 2034/2059* (2016.02); *A61B 2034/2061* (2016.02); *F04C 2270/0421* (2013.01); *G01D 5/2457* (2013.01)

(58) Field of Classification Search
USPC .......................................................... 33/706
See application file for complete search history.

(56) References Cited

U.S. PATENT DOCUMENTS

| | | | | |
|---|---|---|---|---|
| 5,873,835 | A * | 2/1999 | Hastings | A61B 5/0215 600/488 |
| 6,477,396 | B1 * | 11/2002 | Mest | A61B 18/1492 600/374 |
| 7,720,322 | B2 * | 5/2010 | Prisco | G01L 1/246 385/12 |
| 7,815,376 | B2 | 10/2010 | Rogers et al. | |
| 7,930,065 | B2 * | 4/2011 | Larkin | B25J 19/025 600/104 |
| 8,684,253 | B2 * | 4/2014 | Giordano | A61B 17/00234 227/180.1 |
| 2002/0077533 | A1 * | 6/2002 | Bieger | A61B 90/36 600/300 |
| 2003/0217478 | A1 | 11/2003 | Matsumiya et al. | |
| 2004/0015053 | A1 * | 1/2004 | Bieger | A61B 1/00149 600/117 |
| 2005/0015082 | A1 * | 1/2005 | O'Sullivan | A61B 5/0422 606/41 |
| 2005/0081400 | A1 | 4/2005 | Matsumiya et al. | |
| 2005/0090818 | A1 * | 4/2005 | Pike, Jr. | A61B 18/1492 606/41 |
| 2006/0111707 | A1 * | 5/2006 | O'Sullivan | A61B 18/1492 606/41 |
| 2006/0155262 | A1 * | 7/2006 | Kishi | A61B 34/70 606/1 |
| 2007/0208252 | A1 * | 9/2007 | Makower | A61B 5/6851 600/424 |
| 2008/0285909 | A1 | 11/2008 | Younge et al. | |
| 2010/0245846 | A1 | 9/2010 | Yasuda et al. | |
| 2011/0288573 | A1 * | 11/2011 | Yates | A61B 17/07207 606/170 |
| 2011/0295270 | A1 * | 12/2011 | Giordano | A61B 17/00234 606/130 |
| 2012/0116391 | A1 * | 5/2012 | Houser | A61B 17/320092 606/41 |
| 2012/0116393 | A1 * | 5/2012 | Jimenez | A61B 18/12 606/42 |
| 2014/0114327 | A1 * | 4/2014 | Boudreaux | A61B 18/1445 606/130 |
| 2014/0121834 | A1 * | 5/2014 | Ogawa | B25J 3/04 700/257 |
| 2016/0001447 | A1 * | 1/2016 | Iida | A61B 34/37 33/558 |
| 2016/0067450 | A1 * | 3/2016 | Kowshik | A61M 25/0138 604/95.04 |
| 2016/0346924 | A1 * | 12/2016 | Hasegawa | B25J 9/1612 |
| 2016/0374772 | A1 * | 12/2016 | Hasegawa | A61B 1/00 606/130 |

FOREIGN PATENT DOCUMENTS

| | | |
|---|---|---|
| JP | 2003-161639 A | 6/2003 |
| JP | 2004045391 A | 2/2004 |
| JP | 2005087253 A | 4/2005 |
| JP | 2005339916 A | 12/2005 |
| JP | 2008-064208 A | 3/2008 |
| JP | 2008-215911 A | 9/2008 |
| JP | 2010-223723 A | 10/2010 |
| JP | 2010-223725 A | 10/2010 |
| JP | 2011182845 A | 9/2011 |
| WO | WO 2013/010889 A1 | 1/2013 |

OTHER PUBLICATIONS

International Search Report dated Apr. 1, 2014 issued in PCT/JP2013/084394.

* cited by examiner

FIG. 11

|         | SWITCH S1 (INCLUDING FIRST CONTACT MEMBER 49A) | SWITCH S2 (INCLUDING SECOND CONTACT MEMBER 54A) |
|---------|------------------------------------------------|--------------------------------------------------|
| STATE A | OFF                                            | OFF                                              |
| STATE B | OFF                                            | ON                                               |
| STATE C | ON                                             | ON                                               |
| STATE D | ON                                             | OFF                                              |

# POSITION DETECTION SENSOR AND MANIPULATOR

This application is a continuation application based on PCT Patent Application No. PCT/JP2013/084394, filed Dec. 17, 2013, whose priorities are claimed on U.S. Provisional Patent Application No. 61/740,010, filed Dec. 20, 2012, and US Provisional Patent Application No. 61/766,214, filed Feb. 19, 2013. The contents of the PCT Patent Application and the U.S. Provisional Patent Applications are incorporated herein by references.

BACKGROUND OF THE INVENTION

Field of the Invention

The present invention relates to a position detection sensor which detects a position of a linear member, and a manipulator including the position detection sensor.

Description of Related Art

In recent years, studies of medical treatment using robots have been performed to save labor in health-care facilities. In particular, in the field of surgery, there are various suggestions for a manipulator system in which treatment is performed to a patient using a manipulator having multiple degrees of freedom (multiple joints).

For example, a robot surgical system described in U.S. Pat. No. 7,930,065 includes one or more manipulators provided near a surgical table, and a controller which enables an operator to manipulate the manipulator while observing a surgical field. The robot surgical system includes an observation device, and a plurality of treatment tools which are removable from the manipulator.

A main body of the treatment tool is configured in such a manner that a plurality of segments are connected to each other via connection portions. One or more degrees of freedom are given to the manipulator by bending each connection portion. A channel is formed in the main body. An optical fiber is inserted into the channel. A sensor controller is attached to a proximal end portion of the optical fiber.

The optical fiber and the sensor controller are used to detect a bending amount of the main body of the treatment tool. Hereinafter, this is described in detail.

Four cores are arranged in the optical fiber so as to be at the same distance from a central axis of the optical fiber. In a cross section of the optical fiber, these cores are arranged so that the direction in which one of two sets of paired cores faces is orthogonal to the direction in which the other set faces.

In each core, a Fiber Bragg Grating which is a type of diffraction grating is provided at the same position in a longitudinal direction. The sensor controller is connected to two cores in the set. When the optical fiber is bent, one of the two cores in the set becomes longer than the other. The sensor controller can detect this state using the following method.

A mirror which reflects a part of light is attached to a distal end of each core. The sensor controller outputs light having a different wavelength from a proximal end of each core to the distal end thereof. The sensor controller detects an amount of the light reflected and returned by the mirror. Since the amount of the light reflected and returned by the mirror is changed in accordance with a bending amount of the core, the bending amount of the treatment tool into which the optical fiber is inserted can be detected by detecting the amount of the light.

SUMMARY OF THE INVENTION

According to a first aspect of the present invention, a position detection sensor includes: a linear member; a conductive portion and an insulating portion provided in an outer periphery of the linear member and arranged side by side in a direction of an axis of the linear member; a support member having insulating properties and provided so as to be capable of being relatively advanced or retracted in the direction of the axis with respect to the conductive portion and the insulating portion; and a conductive contact member attached to the support member and configured such that a distal end of the contact member comes in contact with outer surfaces of the conductive portion and the insulating portion by a biasing force toward the outer surfaces of the conductive portion and the insulating portion.

According to a second aspect of the present invention, in the position detection sensor according to the first aspect, the conductive portion and the insulating portion may be provided over an entire circumference of the linear member.

According to a third aspect of the present invention, the position detection sensor according to the first aspect or the second aspect may further include: a first biasing member configured to generate the biasing force; a second biasing member configured to generate the biasing force; a holding member configured to hold the first biasing member and the second biasing member; and a fixing portion configured to fix the first biasing member and the second biasing member to the holding member. The first biasing member and the second biasing member may be attached to the support member together with the holding member. The contact member may include a first contact member attached to the first biasing member and a second contact member attached to the second biasing member. The conductive portion may be provided in plural numbers, and the insulating portion may be provided in plural numbers. Each of the plurality of conductive portions and each of the plurality of insulating portions may be alternately arranged in the direction of the axis. The holding member may hold the first biasing member and the second biasing member such that a distance in the direction of the axis between a position in which the second contact member comes in contact with the plurality of conductive portions or the plurality of insulating portions and a position in which the first contact member comes in contact with the plurality of conductive portions or the plurality of insulating portions becomes a predetermined distance.

According to a fourth aspect of the present invention, in the position detection sensor according to the third aspect, a first holding hole extending in the direction of the axis may be formed in the holding member, and the first biasing member may be capable of being inserted into the first holding hole. A rotation prevention portion configured to prevent the first biasing member from rotating around a longitudinal direction of the first biasing member in the first holding hole is provided in the first holding hole.

According to a fifth aspect of the present invention, in the position detection sensor according to the third aspect or the fourth aspect, a length of each of the plurality of conductive portions in the direction of the axis and a length of each of the plurality of insulating portions in the direction of the axis may be equal to each other. When the length of each of the plurality of conductive portions in the direction of the axis is L and N is a natural number, the predetermined distance may be equal to a value obtained using an expression of L(N−1/2).

According to a sixth aspect of the present invention, the position detection sensor according to the first aspect or the second aspect may further include a conductive tubular member which is provided between the conductive portion and the insulating portion, and the linear member, and is electrically connected to the conductive portion. The conductive portion may be provided in plural numbers. The insulating portion may be arranged between the plurality of conductive portions adjacent in the direction of the axis. A length of each of the plurality of conductive portions in the direction of the axis and a length of the insulating portion in the direction of the axis may be set to be substantially equal to each other.

According to a seventh aspect of the present invention, the position detection sensor according to the sixth aspect may further include an insulating covering material which covers the outer periphery of the linear member. The contact member may include a first contact member and a second contact member. A position in which the second contact member comes in contact with the plurality of conductive portions or the insulating portion may be shifted in the direction of the axis by a half of the length of each of the plurality of conductive portions in the direction of the axis relative to a position in which the first contact member comes in contact with the plurality of conductive portions or the insulating portion.

According to an eighth aspect of the present invention, in the position detection sensor according to the sixth aspect, the contact member may include a first contact member and a second contact member. The linear member may have conductivity. The linear member may be electrically connected to the tubular member. A position in which the second contact member comes in contact with the plurality of conductive portions or the insulating portion may be shifted in the direction of the axis by a half of the length of each of the plurality of conductive portions in the direction of the axis relative to a position in which the first contact member comes in contact with the plurality of conductive portions or the insulating portion.

According to a ninth aspect of the present invention, in the position detection sensor according to the sixth aspect, the contact member may include a first contact member formed in a spherical shape and a second contact member formed in a spherical shape. A position in which the second contact member comes in contact with the plurality of conductive portions or the insulating portion may be shifted in the direction of the axis by a half of the length of each of the plurality of conductive portions in the direction of the axis relative to a position in which the first contact member comes in contact with the plurality of conductive portions or the insulating portion.

According to a tenth aspect of the present invention, the position detection sensor according to the sixth aspect may further include a receiving member which includes a concave portion opened toward the axis of the linear member and is formed of a conductive material. The receiving member may be configured to rotatably support the contact member in the concave portion.

According to an eleventh aspect of the present invention, the position detection sensor according to the second aspect may include a second conductive portion arranged side by side in the direction of the axis with the conductive portion and the insulating portion, and a length of the second conductive portion in the direction of the axis may be set to be equal to or more than a length of the conductive portion. The contact member may include a first contact member, a second contact member, a third contact member, and a fourth contact member. A position in which the second contact member comes in contact with the conductive portion, the insulating portion, or the second conductive portion may be shifted to a proximal end of the linear member by a half of the length of the conductive portion in the direction of the axis relative to a position in which the first contact member comes in contact with the conductive portion, the insulating portion, or the second conductive portion. A position in which the third contact member comes in contact with the conductive portion, the insulating portion, or the second conductive portion may be shifted to the proximal end of the linear member by a half of the length of the conductive portion in the direction of the axis relative to the position in which the second contact member comes in contact with the conductive portion, the insulating portion, or the second conductive portion. A position in which the fourth contact member comes in contact with the conductive portion, the insulating portion, or the second conductive portion may be shifted to the proximal end of the linear member by a half of the length of the conductive portion in the direction of the axis relative to the position in which the third contact member comes in contact with the conductive portion, the insulating portion, or the second conductive portion.

According to a twelfth aspect of the present invention, the position detection sensor according to the first aspect may further include a holding member which is provided in the outer periphery of the linear member, and includes a holding surface parallel to the axis of the linear member in an outer surface of the holding member and. The conductive portion and the insulating portion may be arranged on the holding surface. The support member may be configured to be capable of being advanced or retracted in the direction of the axis with respect to the conductive portion and the insulating portion, and may be configured to prevent the linear member from rotating in a circumferential direction with respect to the conductive portion and the insulating portion.

According to a thirteenth aspect of the present invention, a manipulator includes: the position detection sensor according to any one of the first to twelfth aspects; and a pivoting member pivotably supported by the support member. A distal end portion of the linear member is attached to the pivoting member.

BRIEF DESCRIPTION OF THE DRAWINGS

FIG. 11 is a diagram illustrating an ON/OFF state of each switch in states shown in FIGS. 7 to 10.

DETAILED DESCRIPTION OF THE INVENTION (First Embodiment)

Hereinafter, a manipulator system including a position detection sensor and a manipulator according to a first embodiment of the present invention is described with reference to FIGS. 1 to 16.

Figure 1:
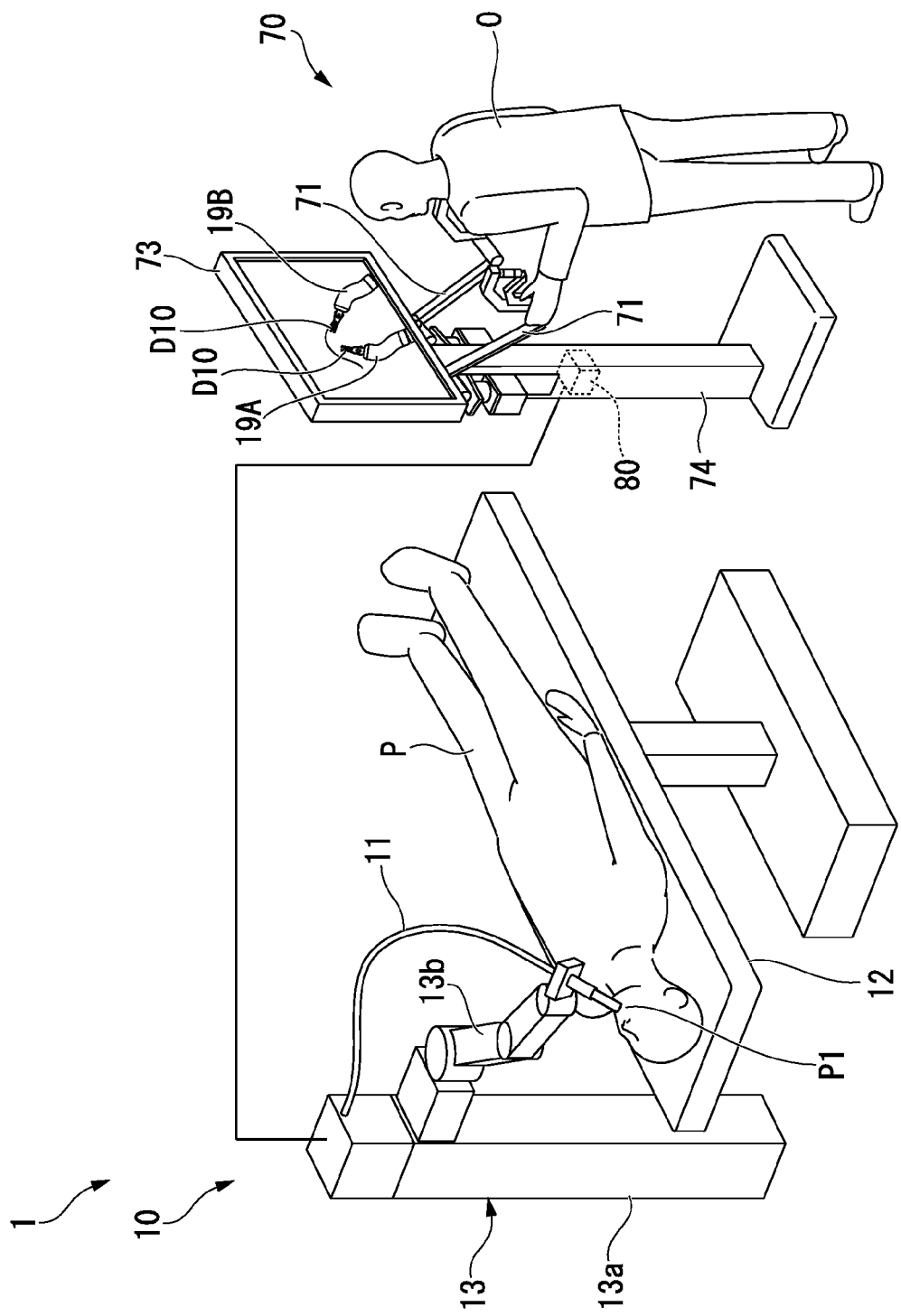
FIG. 1 is an overall view illustrating a manipulator system including a position detection sensor and a manipulator according to a first embodiment of the present invention.
Figure 2:
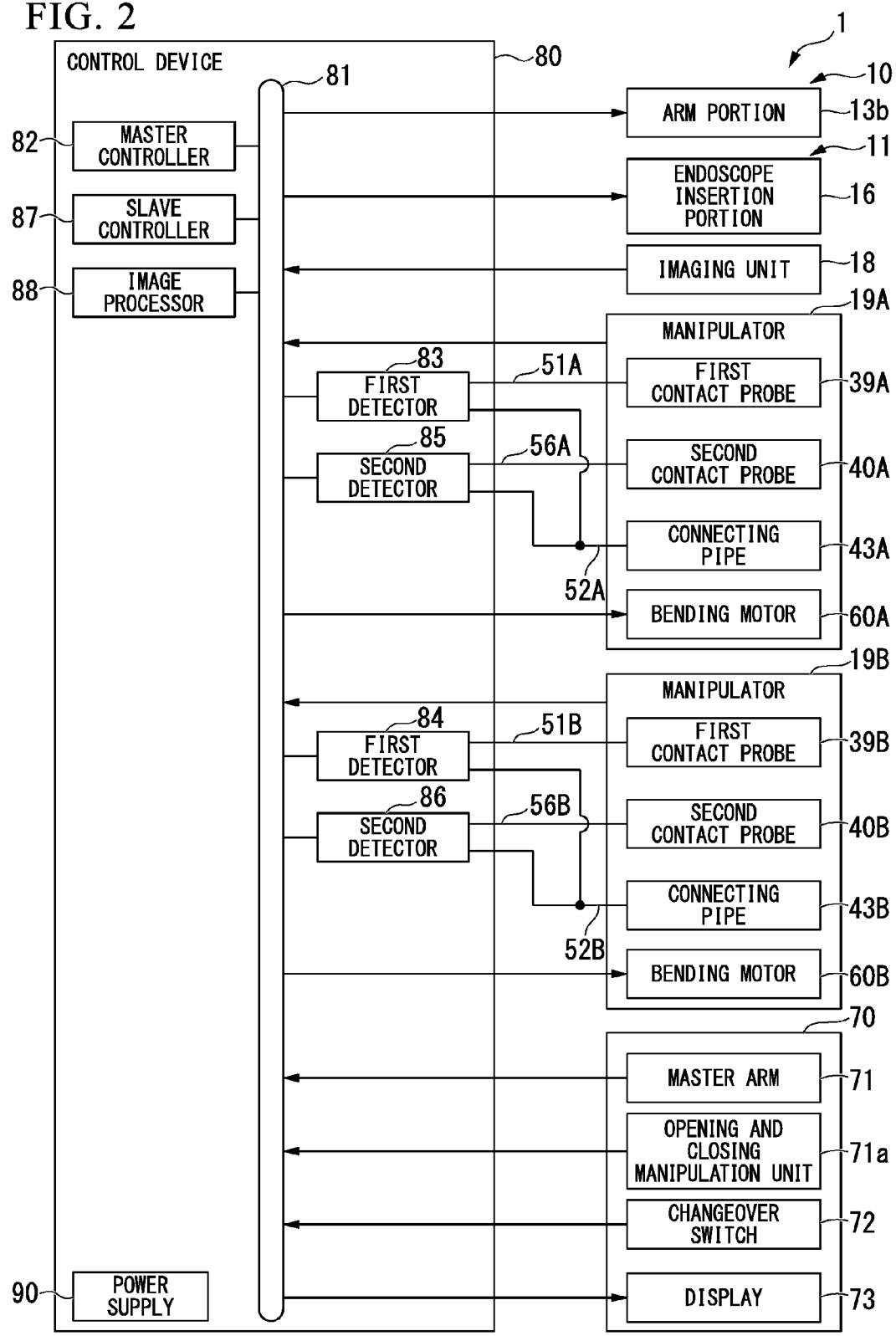
FIG. 2 is a block diagram of the manipulator system.

The manipulator system 1 includes a slave device 10, a master device 70, and a control device 80, as illustrated in FIGS. 1 and 2. An endoscope 11 is provided in the slave device 10. An operator O such as a surgeon manipulates the master device 70 such that the master device 70 gives manipulation information to the control device 80. The control device 80 controls the slave device 10 in accordance with the manipulation information.

The slave device 10 includes a surgical table 12, a multi-joint robot 13, and the above-described endoscope 11, as illustrated in FIG. 1. A patient P is placed on the surgical table 12. The multi-joint robot 13 is disposed near the surgical table 12. The endoscope 11 is attached to the multi-joint robot 13.

The multi-joint robot 13 has a well-known configuration including an arm 13b whose proximal end portion is fixed to a base 13a. The arm 13b has a so-called multi-joint structure. The arm 13b operates in accordance with the manipulation information output from the master device 70.

Figure 3:
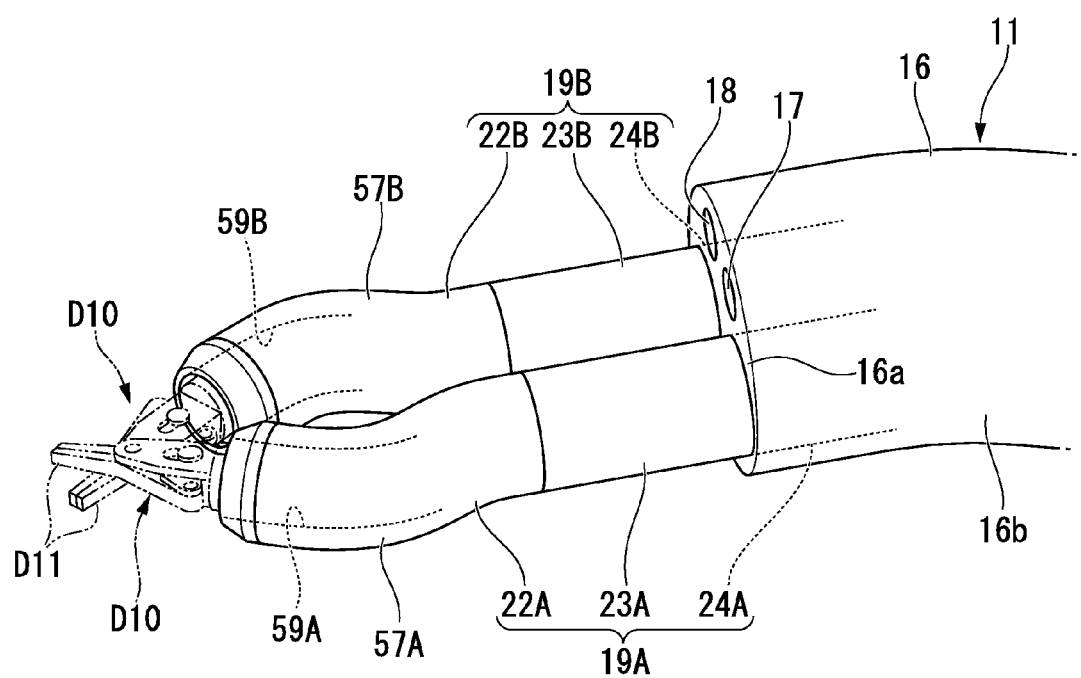
FIG. 3 is a perspective view of a distal end portion in an endoscope of the manipulator system.

The endoscope 11 includes a long flexible endoscope insertion portion 16, as illustrated in FIG. 3. An endoscope bending portion 16b which can be manipulated to be bent is provided in a distal end portion of the endoscope insertion portion 16.

A lighting unit 17 having an LED, an imaging unit 18 having a CCD or the like, and a pair of manipulators 19A and 19B according to the present embodiment are provided in a distal end surface 16a of the endoscope insertion portion 16. The manipulators 19A and 19B are arranged side by side in a radial direction of the endoscope insertion portion 16.

The lighting unit 17 lights ahead of the endoscope insertion portion 16 using power supplied from a power supply 90 (described later). The imaging unit 18 acquires an image from an image such as an observation target, converts the image into a signal, and outputs the signal to the control device 80.

In the present embodiment, the configuration of the manipulator 19A and the manipulator 19B is symmetric with respect to a central axis of the endoscope insertion portion 16. Therefore, the letter "A" is added to a number for the configuration of the manipulator 19A, and the letter "B" is added to the same number for the configuration of the manipulator 19B. Accordingly, repeated explanations are omitted here.

Figure 4:
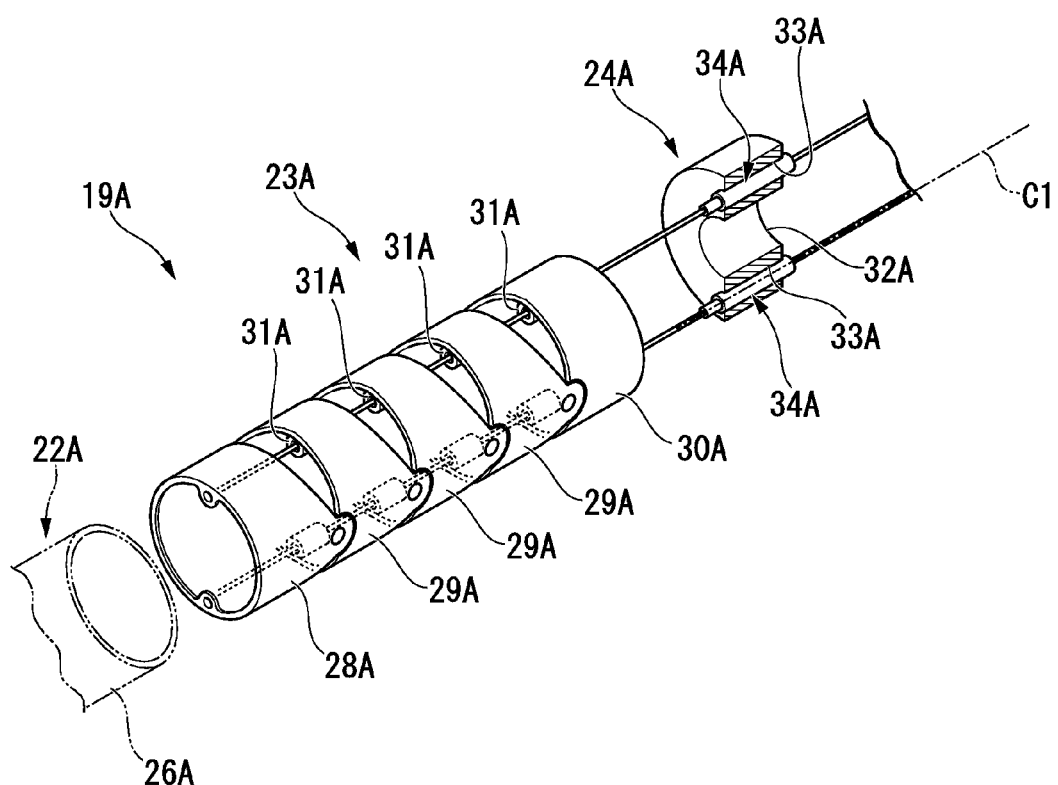
FIG. 4 is a partially cutaway perspective view illustrating an internal configuration of the manipulator of the endoscope.

The manipulator 19A includes a distal end rigid portion 22A, a bending portion 23A, and a bending amount detector 24A, as illustrated in FIGS. 3 and 4. The distal end rigid portion 22A is provided in a distal end portion of the manipulator 19A. The bending portion 23A is provided at a proximal side of the distal end rigid portion 22A, and is configured to be able to be bent and manipulated. The bending amount detector 24A is provided at a proximal side of the bending portion 23A, and configured to detect a bending amount of the bending portion 23A. In FIG. 4, a coating tube 57A (described later) is not illustrated. The manipulator 19A generally includes four position detection sensors 34A (described later) such that the bending portion 23A can be bent in four directions defined at equal angles in the circumferential direction of the bending portion 23A. However, hereinafter, an example in which two position detection sensors 34A are included is described in order to make an explanation easier to understand.

The distal end rigid portion 22A includes a hard portion main body 26A formed of stainless steel or the like in a tubular shape. Although not illustrated in detail, the hard portion main body 26A is formed in a bent shape so that a central part in a longitudinal direction thereof is spaced from the manipulator 19B.

The bending portion 23A includes a distal ring (a pivoting member) 28A, a plurality of bending pieces 29A, and a proximal ring 30A. The distal ring 28A is fixed to the proximal end portion of the hard portion main body 26A. The plurality of bending pieces 29A are pivotably supported in a wall of the distal ring 28A in two places facing in a radial direction with respect to the distal ring 28A. The proximal ring 30A is pivotably supported in two places facing in the radial direction with respect to the bending piece 29A arranged on the most proximal side among the plurality of bending pieces 29A. The bending pieces 29A other than the bending piece 29A arranged on the most distal side among the plurality of bending pieces 29A are pivotably supported with respect to the bending piece 29A arranged on the own distal side. Each guide pipe 31A is provided in the inner peripheries of the bending pieces 29A and the proximal ring 30A.

The bending amount detector 24A includes a ring-shaped member 32A formed of a material having insulation properties such as a resin. A pair of through holes 33A are formed in a wall of the ring-shaped member 32A. The position detection sensor 34A according to the present embodiment is inserted into each of the pair of through holes 33A. The ring-shaped member 32A is fixed to the above-described proximal ring 30A through a fixing member (not illustrated). That is, the distal ring 28A and the bending pieces 29A are pivotably supported by the ring-shaped member 32A.

Figure 5:
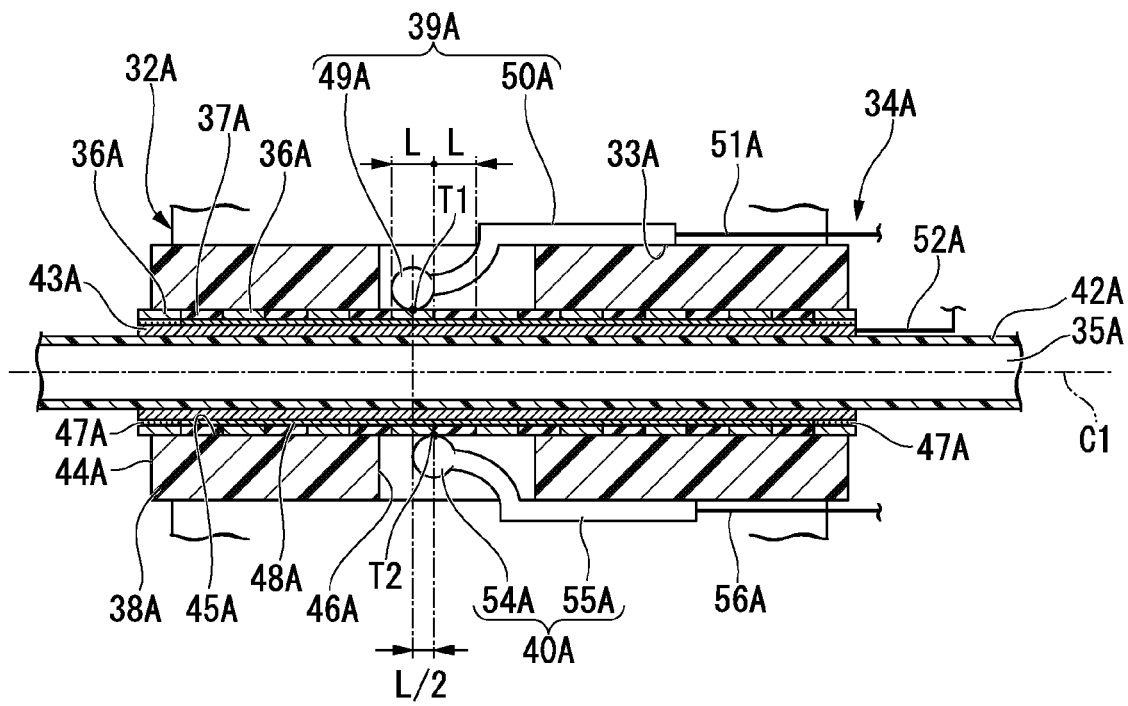
FIG. 5 is a lateral cross-sectional view of the position detection sensor of the manipulator.

The position detection sensor 34A includes a manipulation wire (a linear member) 35A, a plurality of conductive rings (conductive portions) 36A and insulating rings (insulating portions) 37A, a support member 38A, a first contact probe 39A, and a second contact probe 40A, as illustrated in FIG. 5. The plurality of conductive rings 36A and insulating rings 37A are provided on an outer periphery of the manipulation wire 35A. The support member 38A is attached to the conductive rings 36A and the insulating rings 37A. The first contact probe 39A and the second contact probe 40A are attached to the support member 38A.

The manipulation wire 35A is composed of a single wire formed of a metal such as stainless steel, or a stranded wire obtained by twisting a wire. The outer periphery of the manipulation wire 35A is covered with a covering material 42A having electrical insulation properties such as PTFE (polytetrafluoroethylene). A distal end portion of the manipulation wire 35A is fixed to the above-described distal ring 28A illustrated in FIG. 4. The manipulation wire 35A is inserted into the guide pipe 31A and supported by the guide pipe 31A.

The conductive ring 36A and the insulating ring 37A are formed in an annular shape having the same outer diameter and the same inner diameter, as illustrated in FIG. 5. That is, the conductive ring 36A and the insulating ring 37A are formed in a shape which is rotationally symmetric with respect to an axis C1 of the manipulation wire 35A. Lengths (widths) of the conductive ring 36A and the insulating ring 37A in a direction of the axis C1 are set to be substantially equal to each other (may be set to be equal to each other). That is, the lengths of the conductive ring 36A and the insulating ring 37A in the direction of the axis C1 are set to a constant length (a pitch) L. The lengths of the conductive ring 36A and the insulating ring 37A are described in detail later.

The conductive ring 36A is formed of a conductive material such as stainless steel. The insulating ring 37A is formed of a material having electrical insulation properties such as a resin. The insulating ring 37A is arranged between the conductive rings 36A adjacent in the direction of the axis C1, such that the conductive ring 36A and the insulating ring 37A are alternately arranged side by side with no gap in the direction of the axis C1. The conductive ring 36A and the insulating ring 37A are provided over the entire circumference of the manipulation wire 35A.

A connecting pipe (a tubular member) 43A is provided between the plurality of conductive rings 36A and insulating rings 37A and the covering material 42A. That is, the connecting pipe 43A is inserted into the conductive ring 36A and the insulating ring 37A. The connecting pipe 43A is formed of a conductive material such as stainless steel. The connecting pipe 43A is fixed to the covering material 42A using adhesion or caulking in a state in which the manipulation wire 35A is inserted into the connecting pipe 43A. Rings located at both ends in the direction of the axis C1 in the plurality of conductive rings 36A and insulating rings 37A (hereinafter referred to as "the rings 36A and 37A located at both ends") are fixed to the connecting pipe 43A using a conductive adhesive 47A. Accordingly, the conductive ring 36A and the connecting pipe 43A are fixed in a state in which the conductive ring 36A and the connecting pipe 43A are electrically connected. A conductive filling member 48A such as putty is provided between the conductive rings 36A and the insulating rings 37A other than the rings 36A and 37A located at the both ends (hereinafter referred to as "the rings 36A and 37A located in the intermediate part") and the connecting pipe 43A. That is, the rings 36A and 37A located in the intermediate part are not fixed to the connecting pipe 43A, are inserted into the connecting pipe 43A, and are interposed between the rings 36A and 37A located at both ends. In this state, the rings 36A and 37A located in the intermediate part are held to be movable with respect to the connecting pipe 43A.

The support member 38A is formed in a tubular shape. An outer diameter of the support member 38A is set to be slightly smaller than the inner diameter of the through hole 33A of the ring-shaped member 32A. The inner diameter of the support member 38A (a diameter of a cylindrical hole 45A) is set to be slightly larger than the outer diameter of the conductive ring 36A and the insulating ring 37A. The support member 38A has a through hole 46A extending therethrough in a radial direction of the support member 38A and intersecting the cylindrical hole 45A of the support member 38A. It is preferable that the support member 38A is formed of a material having insulation properties and heat resistance, such as ceramics.

The support member 38A is fixed to the ring-shaped member 32A using an adhesive or the like (not illustrated), in a state in which the support member 38A is inserted into the through hole 33A of the ring-shaped member 32A. The manipulation wire 35A in which the conductive ring 36A and the insulating ring 37A are provided is inserted into the cylindrical hole 45A of the support member 38A.

The conductive ring 36A and the insulating ring 37A having the above configurations can be advanced or retracted in the direction of the axis C1 with respect to the support member 38A.

The first contact probe 39A includes a first contact member (a contact member) 49A and a plate spring (a biasing member) 50A. The first contact member 49A is arranged on an outer side in a radial direction of the conductive ring 36A and the insulating ring 37A, and is configured to be able to come in contact with outer peripheries of the conductive ring 36A and the insulating ring 37A in a point form. The plate spring 50A biases the first contact member 49A to the outer periphery of the conductive ring 36A and the insulating ring 37A.

The first contact member 49A is formed of a conductive material such as stainless steel in a spherical shape. The point form mentioned herein is not a point in a mathematical sense but indicates that a length of a portion in which the outer peripheries of the conductive ring 36A and the insulating ring 37A and the first contact member 49A come in contact with each other in the direction of the axis C1 is sufficiently shorter than the length of the conductive ring 36A and the insulating ring 37A in the direction of the axis C1. Specifically, it is preferable that the length of the contacting portion in the direction of the axis C1 is $1/1000$ or more and $1/10$ or less of the length L of the conductive ring 36A and the insulating ring 37A in the direction of the axis C1. The first contact member 49A is arranged closer to the inner periphery side of the ring-shaped member 32A than the manipulation wire 35A in the through hole 46A.

One end of the plate spring 50A is attached to the outer periphery of the support member 38A, and the other end of the plate spring 50A is attached to the first contact member 49A. The plate spring 50A is formed of the same material as the first contact member 49A, and it is preferable that the plate spring 50A is formed integrally with the first contact member 49A. The plate spring 50A extends from the first contact member 49A to the proximal end. The first contact member 49A is held in a state in which the first contact member 49A comes in contact with the outer periphery of the conductive ring 36A or the insulating ring 37A by the plate spring 50A.

The wiring 51A is connected to the plate spring 50A of the first contact probe 39A, as illustrated in FIGS. 2 and 5. The wiring 52A is connected to the connecting pipe 43A. The wiring 51A and the wiring 52A are connected to the control device 80.

The second contact probe 40A is configured like the first contact probe 39A. Specifically, the second contact member (a contact member) 54A and the plate spring (a biasing member) 55A included in the second contact probe 40A have the same configuration as the first contact member 49A and the plate spring 50A of the first contact probe 39A, as illustrated in FIG. 5. However, a position T2 in which the second contact member 54A comes in contact with the conductive ring 36A or the insulating ring 37A is shifted to the proximal end by a half of the length L relative to a position T1 in which the first contact member 49A comes in contact with the conductive ring 36A or the insulating ring 37A.

The wiring 56A connected to the plate spring 55A of the second contact probe 40A is connected to the control device 80, as illustrated in FIGS. 2 and 5.

In the position detection sensor 34A having the above configuration, when the manipulation wire 35A is moved to the distal side (pushed) or moved to the proximal side (retracted) with respect to the support member 38A, the rings 36A and 37A located in the intermediate part project to the distal side or the proximal side with respect to the support member 38A. The rings 36A and 37A located in the intermediate part are not fixed to the connecting pipe 43A. Therefore, a portion in which the rings 36A and 37A located in the intermediate part are provided can be easily bent in this state.

When the rings 36A and 37A located in the intermediate part are not moved until projecting from the support member 38A or when the portion in which the rings 36A and 37A located in the intermediate part are provided is not bent, the rings 36A and 37A located in the intermediate part may be fixed to the connecting pipe 43A.

The ring-shaped member 32A and the support member 38A of the position detection sensor 34A are different members, and the support member 38A is fixed to the ring-shaped member 32A. Through this configuration, the position detection sensor 34A can be easily attached to the manipulator 19A.

The hard portion main body 26A, the distal ring 28A, the bending pieces 29A, and the proximal ring 30A are covered with the coating tube 57A illustrated in FIG. 3.

In the manipulator 19A, a channel 59A illustrated in FIG. 3 is configured of a conduit line of the hard portion main body 26A, an internal space of the distal ring 28A, internal spaces of the bending pieces 29A, an internal space of the proximal ring 30A, and a cylindrical hole of the support member 38A.

A bending motor 60A (see FIG. 2) is connected to the proximal end portion of each of the pair of manipulation wires 35A provided in the manipulator 19A. As one of the pair of bending motors 60A retracts the manipulation wire 35A, the bending portion 23A of the manipulator 19A can be bent in a desired direction.

The channel 59A is configured so that a well-known treatment tool such as a forceps D10 can be inserted into the channel 59A. The forceps D10 is configured so that an opening and closing operation for causing a pair of forceps pieces D11 provided in the distal end portion of the forceps D10 to be spaced from each other and to approach each other can be performed. The forceps D10 is configured to be able to be advanced or retracted in the channel 59A and to be able to be rotated about its own axis. With a manipulation of the master device 70, the operations of opening and closing, advancing and retracting, and rotation of the pair of forceps pieces D11 in the forceps D10 can be performed.

The master device 70 includes a pair of master arms 71, a changeover switch 72, and a display 73, as illustrated in FIGS. 1 and 2. The pair of master arms 71 are moved by the operator O. The changeover switch 72 switches a target manipulated with the master arm 71. The display 73 displays an image or the like acquired by the imaging unit 18 of the endoscope 11.

The master arm 71 is a manipulation unit provided to manipulate the arm 13b of the multi-joint robot 13, the endoscope insertion portion 16, and the manipulators 19A and 19B (hereinafter referred to as "the manipulator 19A or the like"). The pair of master arms 71 correspond to a right hand and a left hand of the operator O. The master arm 71 has a multi joint structure to control the manipulator 19A or the like having a multi-joint structure.

The proximal end portion of the master arm 71 is attached to the support stand 74. An opening and closing manipulation unit 71a (see FIG. 2) for opening and closing the pair of forceps pieces D11 of the forceps D10 is provided in a distal end portion located in a side of the operator O in the master arm 71. The pair of master arms 71 and the opening and closing manipulation unit 71a output manipulation information to the control device 80 when manipulated.

The changeover switch 72 switches the target manipulated with the master arm 71 between the manipulator 19A and the like. The changeover switch 72 outputs one or two selected from among the manipulator 19A or the like as selection information.

The display 73 can display an image acquired by the imaging unit 18 of the endoscope 11. When the endoscope 11 is inserted into a body of the patient P, the manipulators 19A and 19B and the forceps D10 are displayed on the display 73 together with a target tissue. In the present embodiment, for example, the display 73 is provided on an upper end of the support stand 74.

The control device 80 includes a master controller 82, first detectors 83 and 84, second detectors 85 and 86, a slave controller 87, an image processor 88, and a power supply 90, as illustrated in FIG. 2. Each of the master controller 82, the first detectors 83 and 84, the second detectors 85 and 86, the slave controller 87, and the image processor 88 is connected to a bus 81.

The arm 13b of the multi joint robot 13, the endoscope insertion portion 16 of the endoscope 11, the imaging unit 18, the manipulators 19A and 19B, the master arm 71 of the master device 70, the opening and closing manipulation unit 71a, the changeover switch 72, and the display 73 are connected to the bus 81.

Each of the master controller 82, the first detectors 83 and 84, the second detectors 85 and 86, the slave controller 87, and the image processor 88 includes a calculation element, a memory, and a control program.

The master controller 82 calculates a command value of a position and an orientation of the distal end of the manipulator 19A or the like in accordance with the manipulation information output from the master arm 71, for a device corresponding to the selection information output from the changeover switch 72 among the manipulator 19A or the like. The master controller 82 outputs the calculated command value to the slave controller 87.

Figure 6:
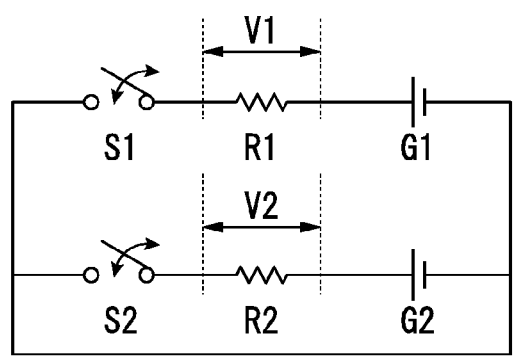
FIG. 6 is a diagram illustrating an equivalent circuit of the position detection sensor, a first detector, and a second detector.

The first detector 83 includes a voltage generator and a resistor (see FIG. 6). The wirings 51A and 52A are connected to the first detector 83. The first detector 83 measures a potential difference generated between both ends of the resistor when a current flows between the first contact probe 39A of the manipulator 19A and the connecting pipe 43A. Accordingly, the first detector 83 can detect a conduction state (ON) in which the first contact probe 39A and the connecting pipe 43A are electrically connected or a blocking state (OFF) in which the first contact probe 39A and the connecting pipe 43A are electrically insulated. When the first contact member 49A of the first contact probe 39A and the conductive ring 36A come in contact with each other, the first detector 83 detects the conduction state. When the first contact member 49A and the conductive ring 36A do not come in contact with each other, the first detector 83 detects the blocking state.

Values of the lengths L or the like of the conductive ring 36A and the insulating ring 37A described above are stored in the memory of the slave controller 87.

The second detector 85 is configured like the first detector 83. Wirings 56A and 52A are connected to the second detector 85.

A relation among the position detection sensor 34A, the first detector 83, and the second detector 85 of the manipulator system 1 having the above configuration is expressed by an equivalent circuit illustrated in FIG. 6. A switch S1 is configured of the first contact probe 39A, the conductive ring 36A, and the insulating ring 37A. A switch S2 is configured of the second contact probe 40A, the conductive ring 36A, and the insulating ring 37A.

When the first contact probe 39A and the conductive ring 36A come in contact with each other and the switch S1 enters the conduction state, a potential difference V1 is generated between both ends of a resistor R1 by a voltage generator G1 provided in the first detector 83. The switch S1 entering the conduction state is determined by determining whether the potential difference V1 exceeds a threshold stored in the memory. For the switch S2, similarly, the switch S2 entering the conduction state is determined by a potential difference V2 generated between both ends of a resistor R2 by a voltage generator G2 provided in the second detector 85.

Figure 7:
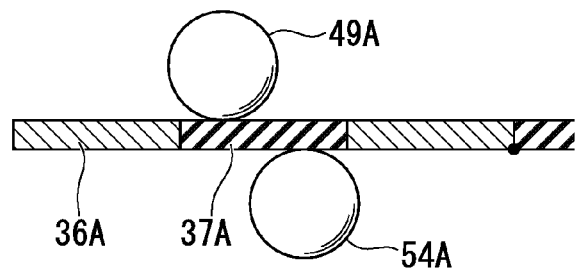
FIG. 7 is a schematic view illustrating a relation of positions of a conductive ring and an insulating ring with respect to a contact member of the position detection sensor.
Figure 8:
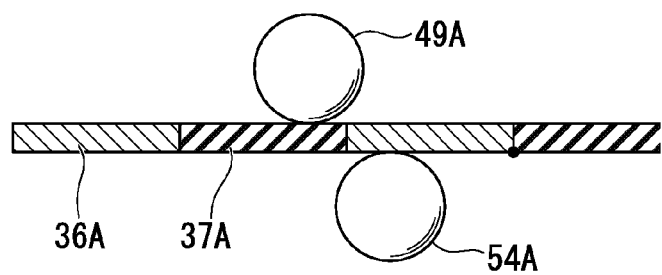
FIG. 8 is a schematic view illustrating a relation of positions of the conductive ring and the insulating ring with respect to the contact member of the position detection sensor.
Figure 9:
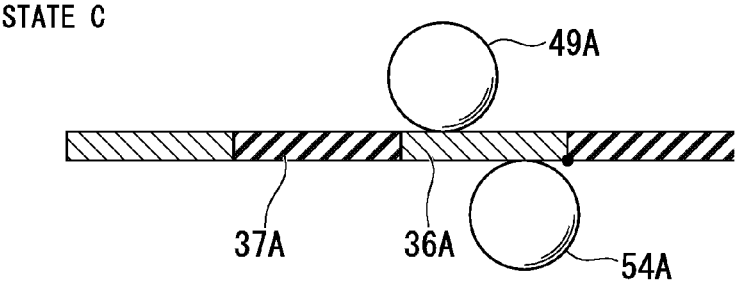
FIG. 9 is a schematic view illustrating a relation of positions of the conductive ring and the insulating ring with respect to the contact member of the position detection sensor.
Figure 10:
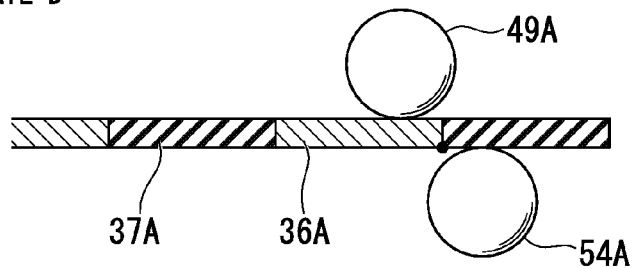
FIG. 10 is a schematic view illustrating a relation of positions of the conductive ring and the insulating ring with respect to the contact member of the position detection sensor.

When the manipulation wire 35A is pushed at a constant speed with respect to the support member 38A, positions of the rings 36A and 37A with respect to the contact members 49A and 54A are successively changed from the state A illustrated in FIG. 7 to the state B illustrated in FIG. 8 to the state C illustrated in FIG. 9 then to the state D illustrated in FIG. 10. ON/OFF states of the switches S1 and S2 in the state A to the state D are illustrated in FIG. 11. When the positions of the rings 36A and 37A with respect to the contact members 49A and 54A enter the state B illustrated in FIG. 8 through pushing of the manipulation wire 35A in a state in which the switches S1 and S2 are OFF in the state A illustrated in FIG. 7, the switch S2 becomes ON. When the manipulation wire 35A is further pushed and the positions of the rings 36A and 37A with respect to the contact members 49A and 54A enter the state C illustrated in FIG. 9, the switch S1 becomes ON. When the manipulation wire 35A is further pushed and the positions of the rings 36A and 37A with respect to the contact members 49A and 54A enter the state D illustrated in FIG. 10, the switch S2 becomes OFF. When the manipulation wire 35A is further pushed and the positions of the rings 36A and 37A with respect to the contact members 49A and 54A enter the state A illustrated in FIG. 7, the switch S1 becomes OFF.

Figure 12:
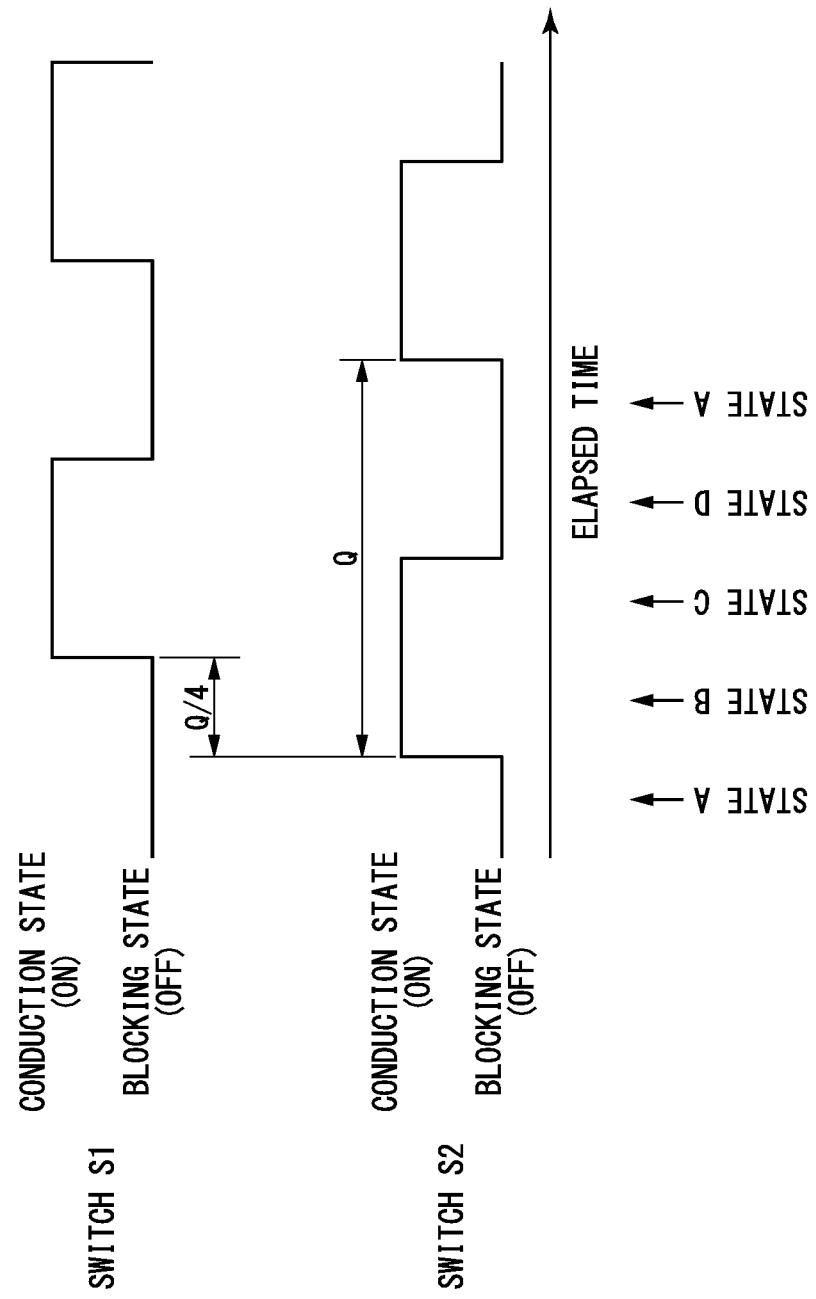
FIG. 12 is a diagram illustrating a timing at which a conduction state and a blocking state of each switch are switched when a manipulation wire of the position detection sensor is pushed.

When the manipulation wire 35A is pushed to the distal side at a constant speed with respect to the support member 38A, the conduction state (ON) and the blocking state (OFF) of each of the switches S1 and S2 are switched over an elapsed time, as illustrated in FIG. 12. A time required for the position T1 with which the first contact member 49A comes in contact to pass through a set of the conductive ring 36A and the insulating ring 37A in the direction of the axis C1 is a period Q. In this case, the conduction state and the blocking state of the switch S1 are switched with delay of ¼ of the period Q with respect to timing at which the conduction state and the blocking state of the switch S2 are switched. Thus, when the manipulation wire 35A is pushed, a change from the state A to the state D performed in the period Q is repeatedly performed.

Figure 13:
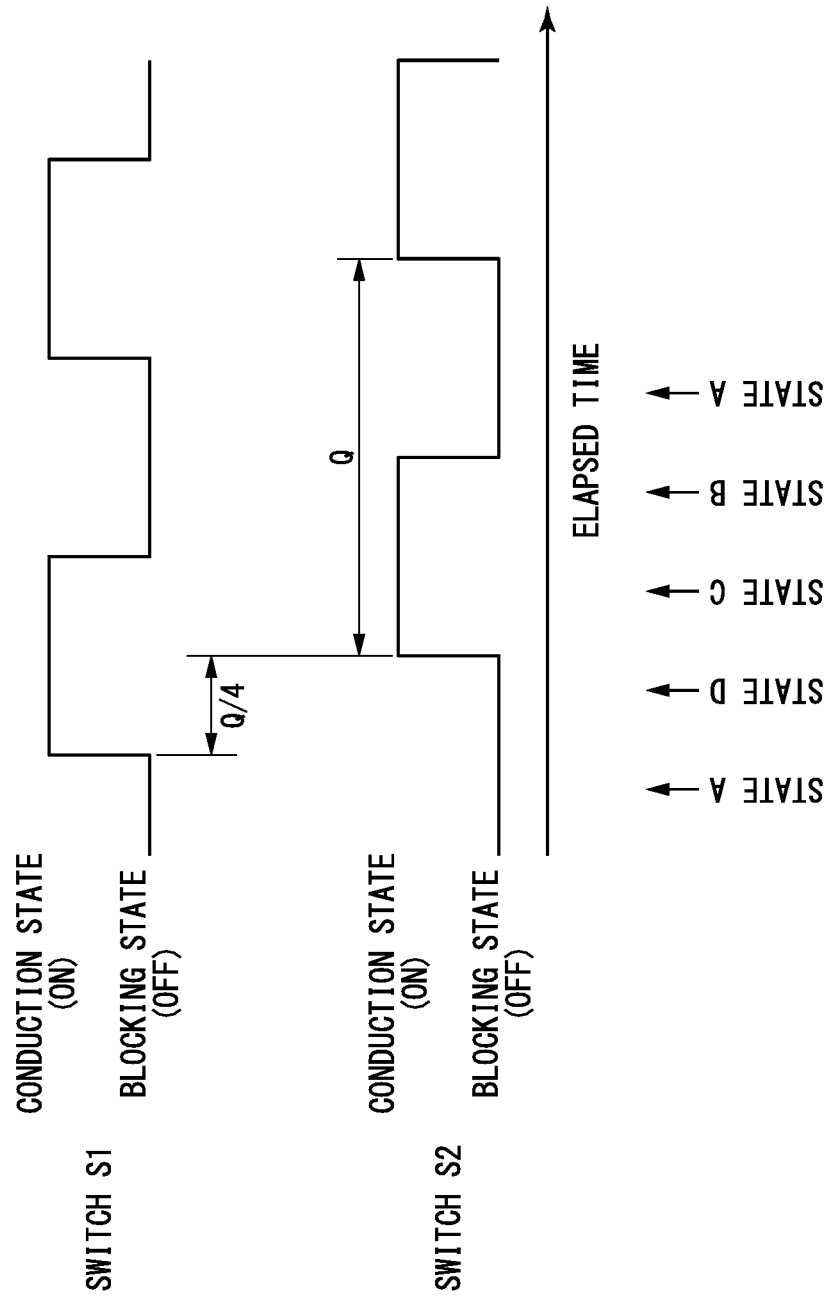
FIG. 13 is a diagram illustrating a timing at which the conduction state and the blocking state of each switch are switched when the manipulation wire of the position detection sensor is retracted.

On the other hand, when the manipulation wire 35A is retracted with respect to the support member 38A, a repetitive change occurs in order of the state D, the state C, the state B, and the state A. The conduction state and the blocking state of each of the switches S1 and S2 are switched over the elapsed time as illustrated in FIG. 13. That is, the conduction state and the blocking state of the switch S1 are switched faster by ¼ of the period Q with respect to the timing at which the conduction state and the blocking state of the switch S2 are switched. Thus, switching of ON/OFF signals of the switches S1 and S2 when the manipulation wire 35A is pushed at the constant speed differs from that when the manipulation wire 35A is retracted at the constant speed.

For example, when the manipulation wire 35A is recognized as being pushed, a length by which the manipulation wire 35A is pushed can be calculated by multiplying the number of times when the switch S1 becomes ON by twice the length L. The same applies when the manipulation wire 35A is retracted.

As the manipulation wire 35A is pushed and retracted, the bending portion 23A is bent. A position of the manipulation wire 35A with respect to the support member 38A in the direction of the axis C1 corresponds one-to-one with a bending amount of the bending portion 23A.

The first detector 83 and the second detector 85 output a signal indicating the conduction state or the blocking state for the switches S1 and S2 of the manipulator 19A to the slave controller 87.

The first detector 84 and the second detector 86 are provided to correspond to the first detector 83 and the second detector 85, for the manipulator 19B, respectively. The first detector 84 and the second detector 86 output a signal indicating the conduction state or the blocking state for the switches S1 and S2 of the manipulator 19B to the slave controller 87.

The slave controller 87 detects whether the manipulation wire 35A is pushed or retracted by a shift of switching timing between the switches S1 and S2 in the signals output from the first detector 83 and the second detector 85 for the manipulator 19A. The slave controller 87 calculates the position of the manipulation wire 35A in the direction of the axis C1 with respect to the support member 38A by counting the number of times of the conduction state and performing a process as described above.

A table indicating a correspondence relation between the position of the manipulation wire 35A and the bending amount of the bending portion 23A is stored in the memory of the slave controller 87 in advance. The calculation element of the slave controller 87 calculates the bending amount of the bending portion 23A from the table and outputs the bending amount to the display 73. Similarly, for the manipulator 19B, the bending amount of the bending portion 23B is calculated and output to the display 73. The output bending amount of each of the manipulators 19A and 19B is displayed on the display 73.

The slave controller 87 calculates, through reverse kinematics calculation, a driving amount of a joint of the manipulator 19A or the like necessary to match the command value of the position and the orientation of the distal end of the manipulator 19A or the like, based on the command value of the position and the orientation calculated by the master controller 82 and the selection information output from the changeover switch 72. The slave controller 87 drives the manipulator 19A or the like based on the calculation result. When the slave controller 87 drives the manipulators 19A and 19B, the slave controller 87 manipulates the manipulation wires 35A and 35B using the bending motors 60A and 60B and bends the bending portions 23A and 23B.

The image processor 88 appropriately converts the image signal output from the imaging unit 18 and outputs the resultant signal to the display 73.

The power supply 90 supplies power input from the outside to the slave device 10, the master device 70, the master controller 82, and the like.

In the present embodiment, for example, the control device 80 is provided in the support stand 74, as illustrated in FIG. 1.

A method of manufacturing the position detection sensor 34A in the manipulator system 1 configured as above is described. Here, a process of attaching, particularly, the connecting pipe 43A, the conductive ring 36A, and the insulating ring 37A to the manipulation wire 35A in the position detection sensor 34A is described.

Figure 14:
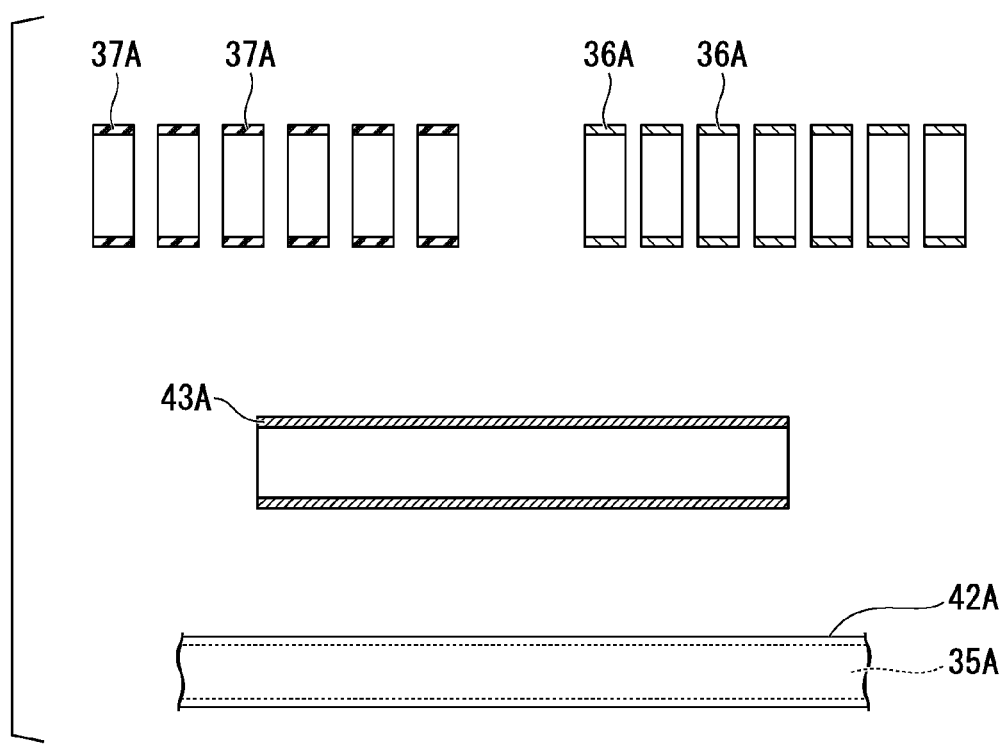
FIG. 14 is a diagram illustrating a method of manufacturing the position detection sensor.

The connecting pipe 43A, the plurality of conductive rings 36A and insulating rings 37A, and the manipulation wire 35A are prepared as illustrated in FIG. 14. The manipulation wire 35A is coated with the covering material 42A using a well-known method in advance.

Figure 15:
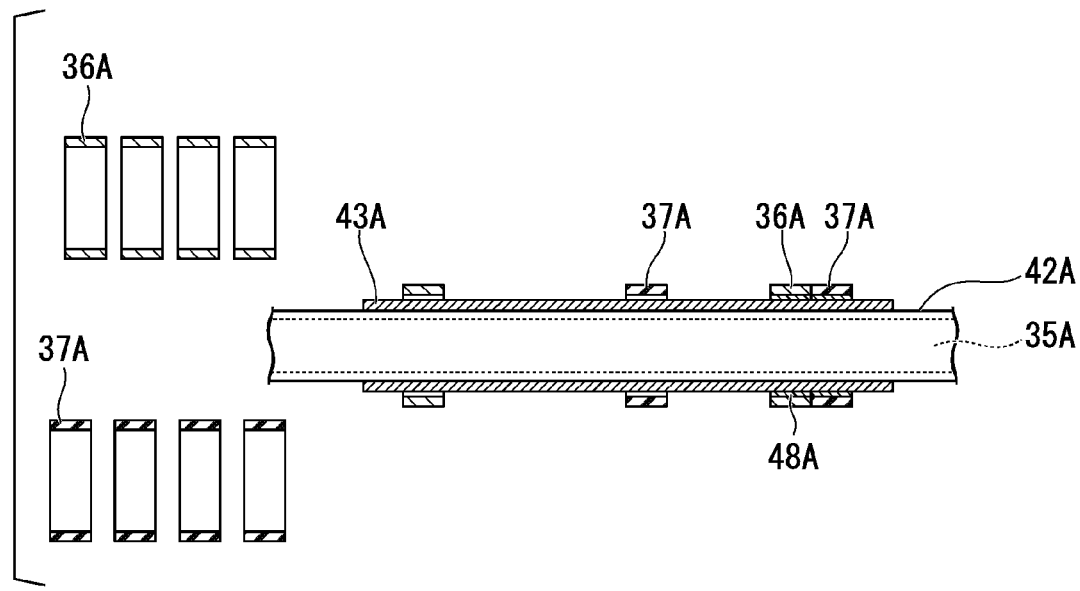
FIG. 15 is a diagram illustrating the method of manufacturing the position detection sensor.

As illustrated in FIG. 15, the manipulation wire 35A is inserted into the connecting pipe 43A, and the connecting pipe 43A is fixed to the covering material 42A using adhesion or caulking. The connecting pipe 43A is inserted into the rings 36A and 37A located in the intermediate part such that the rings 36A and 37A are alternately arranged. Then, the filling member 48A is provided between the rings 36A and 37A and the connecting pipe 43A.

Figure 16:
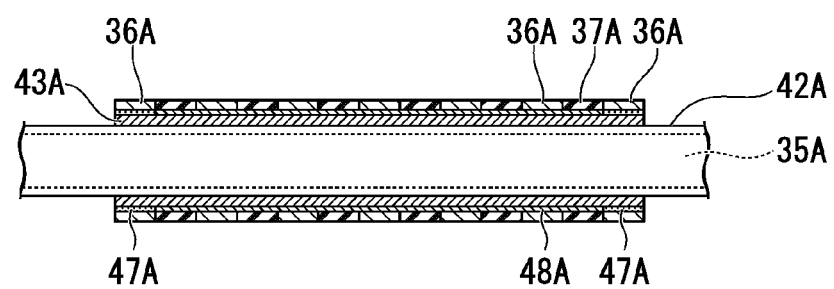
FIG. 16 is a diagram illustrating the method of manufacturing the position detection sensor.

The connecting pipe 43A is inserted into the rings 36A and 37A located at both ends, as illustrated in FIG. 16. The rings 36A and 37A and the connecting pipe 43A are fixed to each other with the adhesive 47A.

Next, a procedure using the manipulator system 1 configured as described above is described focusing on operation of the position detection sensor 34A. Hereinafter, a case in which a target tissue formed in a stomach wall is treated is described. A target portion is not limited thereto, and may be, for example, a hollow organ such as an esophagus, a duodenum, a small intestine, a large intestine, a uterus, or a bladder.

An assistant lays a patient P down on the surgical table 12 as illustrated in FIG. 1. The assistant performs appropriate treatment such as disinfection or anesthesia on the patient P. When the manipulator system 1 starts up, power is supplied from the power supply 90 to the slave device 10, the master device 70, the master controller 82, and the like.

As the power from the power supply 90 is supplied to the lighting unit 17, the front of the endoscope insertion portion 16 is lit. The operator O confirms an image of the front of the endoscope insertion portion 16 acquired by the imaging unit 18 on the display 73.

The operator O arranges the forceps D10 so that the forceps D10 does not project from the distal ends of the manipulators 19A and 19B. The operator O switches the changeover switch 72 such the manipulators 19A and 19B can be manipulated by the master arm 71. The operator O manipulates the master arm 71 to manipulate the manipulation wires 35A and 35B using the bending motors 60A and 60B such that the bending portions 23A and 23B are not bent and an entire width of the manipulators 19A and 19B is small, as illustrated in FIG. 3.

Here, for example, for the manipulator 19A, the conduction state and the blocking state of each of the switches S1 and S2 are detected by the first detector 83 and the second detector 85, as described above. The signals are output to the slave controller 87.

The conductive ring 36A and the insulating ring 37A are formed in rotational symmetry with respect to the axis C1. Therefore, even when the rings 36A and 37A are rotated about the axis C1 with respect to the first contact member 49A, there is no influence on the detection result of the conduction state or the blocking state of the switch S1.

The signal is processed by the slave controller 87. The bending amounts of the bending portions 23A and 23B is displayed on the display 73. The operator O stops driving of the bending motors 60A and 60B when the bending portions 23A and 23B are in a straight state (when the bending amounts become 0) while checking the bending amounts on the display 73.

Figure 17:
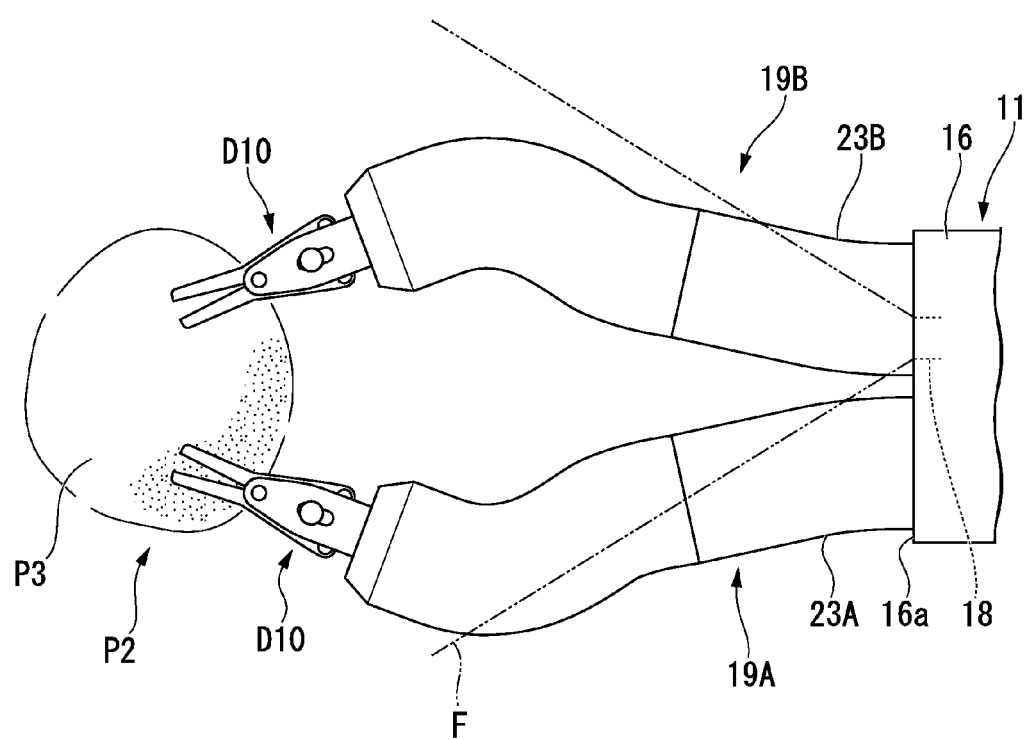
FIG. 17 is a diagram illustrating a procedure using the manipulator system.

The operator O switches the changeover switch 72 such that the arm 13b of the multi-joint robot 13 and the endoscope insertion portion 16 can be manipulated by the master arm 71. The operator O manipulates the master arm 71 to drive the arm 13b. The operator O introduces the endoscope insertion portion 16 of the endoscope 11 into a stomach through a mouth P1 of the patient P. The operator O causes the distal end surface 16a of the endoscope insertion portion 16 to face a target tissue P3 formed in the stomach wall P2 while appropriately bending the endoscope bending portion 16b, and holds a position of the endoscope insertion portion 16, as illustrated in FIG. 17.

The operator O causes the forcipes D10 to project from the distal ends of the manipulators 19A and 19B. The operator O switches the changeover switch 72 such that the manipulators 19A and 19B can be manipulated by the master arm 71. The operator O manipulates the master arm 71 to bend the bending portions 23A and 23B for a so-called arrangement of triangulation in which a pair of forcipes D10 substantially face each other in a field of view F in front of the imaging unit 18.

Thereafter, the operator O performs appropriate treatment on the target tissue P3 using the forcipes D10 or the like and ends a series of procedures.

According to the position detection sensor 34A and the manipulator 19A according to the present embodiment, the state in which the first contact member 49A comes in contact with the conductive ring 36A or the insulating ring 37A is held by the plate spring 50A. A relative position of the first contact member 49A and the manipulation wire 35A in the direction of the axis C1 can be detected by detecting the conduction state or the blocking state between the conductive ring 36A and the first contact member 49A.

When the conductive ring 36A and the first contact member 49A are in the conduction state, the manipulation wire 35A and the first contact member 49A are determined to be in a position in which the conductive ring 36A and the first contact member 49A come in contact with each other. On the other hand, when the conductive ring 36A and the first contact member 49A are in the blocking state, the manipulation wire 35A and the first contact member 49A are determined to be in a position in which the conductive ring 36A and the first contact member 49A do not come in contact with each other and the insulating ring 37A and the first contact member 49A come in contact with each other.

Thus, the positions of the first contact member 49A and the manipulation wire 35A provided with the conductive ring 36A in the direction of the axis C1 are detected by detecting the conduction state or the blocking state between the conductive ring 36A and the first contact member 49A. The position of the manipulation wire 35A in the direction of the axis C1 corresponds one-to-one with the bending amount of the bending portion 23A. Therefore, the bending amount of the bending portion 23A is determined from the detected position of the manipulation wire 35A.

As only the conductive ring 36A, the insulating ring 37A, the support member 38A, and the first contact probe 39A are provided to the manipulation wire 35A necessary for a bending manipulation of the bending portion 23A, the position detection sensor 34A can be configured with a small size and simply. Particularly, a portion closer to the distal end of the manipulation wire 35A than the conductive ring 36A, the insulating ring 37A, the support member 38A, and the first contact probe 39A is configured of only the manipulation wire 35A. Through this configuration, the outer diameter of the position detection sensor 34A can be reduced.

The conductive ring 36A and the insulating ring 37A are provided over the entire circumference of the manipulation wire 35A. Therefore, the conduction state and the blocking state of each of the switches S1 and S2 can be reliably detected even when the manipulation wire 35A rotates about the axis C1.

The position detection sensor 34A includes the plurality of conductive rings 36A and insulating rings 37A arranged side by side in the direction of the axis C1. The number of times when the conduction state occurs when the manipulation wire 35A is pushed is calculated to obtain the position of the manipulation wire 35A in accordance with the number of times, so that the position of the manipulation wire 35A in the direction of the axis C1 can be accurately detected.

Since the connecting pipe 43A electrically connected to each conductive ring 36A is included, the conduction state of each conductive ring 36A can be easily detected by connecting the first detector 83 and the second detector 85 to the connecting pipe 43A.

It is possible to suppress delivery of external electromagnetic noise to the manipulation wire 35A by covering the manipulation wire 35A with the insulating covering material 42A.

The position T2 in which the second contact member 54A comes in contact is shifted to the proximal end by a half of the length L relative to the position T1 in which the first contact member 49A comes in contact. Accordingly, the manipulation wire 35A being pushed or retracted can be determined by comparing the signals indicating the conduction state or the blocking state for the switches S1 and S2.

The manipulator 19A includes the position detection sensor 34A, such that the outer diameter of the bending portion 23A can be reduced.

Figure 18:
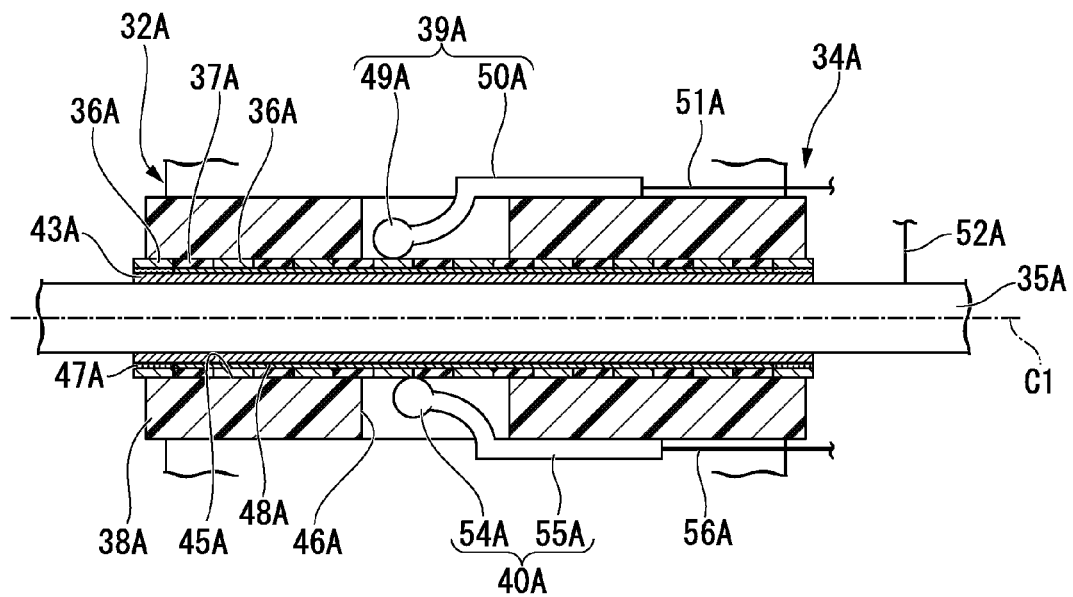
FIG. 18 is a lateral cross-sectional view of the position detection sensor in a modified example of the position detection sensor according to the first embodiment of the present invention.

In the present embodiment, the position detection sensor 34A may not include a covering material 42A, as illustrated in FIG. 18. In this case, the manipulation wire 35A and the connecting pipe 43A are electrically connected by conductive adhesion or caulking. The distal end of the wiring 52A is connected to the manipulation wire 35A.

According to the position detection sensor 34A having the above configuration, the connecting pipe 43A can be electrically connected to the first detector 83 and the second detector 85 through the manipulation wire 35A. Therefore, the length of the wiring 52A can be shortened, and manufacturing cost of the position detection sensor 34A can be reduced.

In a modified example, a covering material 42A may be provided in a portion of the manipulation wire 35A in which the connecting pipe 43A is not provided or a portion thereof in which the wiring 52A is not connected.

In the present embodiment, the position T2 in which the second contact member 54A comes in contact is shifted to the proximal end by a half of the length L relative to the position T1 in which the first contact member 49A comes in contact. However, this position T2 may be shifted to the distal end by a half of the length L relative to the position T1.

In the present embodiment, the position detection sensor 34A includes the plurality of conductive rings 36A and insulating rings 37A. However, the position detection sensor 34A may include at least one of each of the conductive ring 36A and the insulating ring 37A. Even in this case, the conduction state between the conductive ring 36A and the first contact member 49A is detected, such that the positions of the manipulation wire 35A and the first contact member 49A in the direction of the axis C1 can be detected.

The support member 38A of a pair of position detection sensors 34A is fixed to the ring-shaped member 32A. However, the pair of support members 38A may be formed in the same shape as the ring-shaped member 32A as a whole, and may be used in place of the ring-shaped member 32A. In this case, the contact probes 39A and 40A are attached to a support member (a ring-shaped member).

In the present embodiment, the linear member which is the manipulation wire 35A is formed of a metal. However, the linear member may be formed of a hard resin.

(Second Embodiment)

A second embodiment of the present invention is described with reference to FIG. 19. In the present embodiment, the same portions as those in the above embodiment are denoted with the same reference signs and a description thereof is omitted, and only differences are described.

Figure 19:
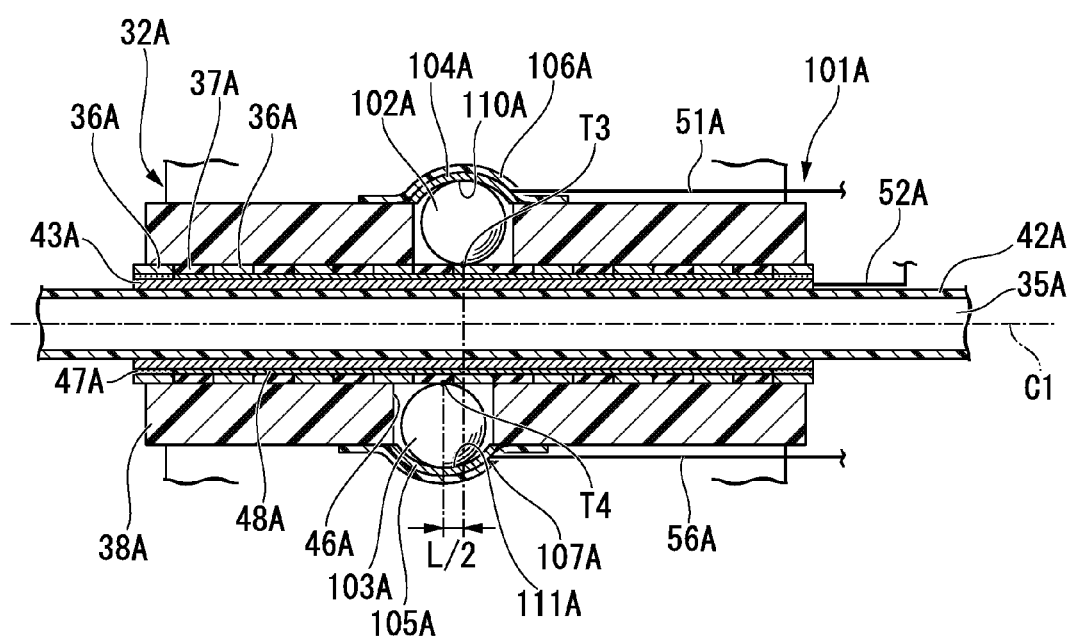
FIG. 19 is a lateral cross-sectional view of a position detection sensor according to a second embodiment of the present invention.

As illustrated in FIG. 19, a position detection sensor 101A according to the present embodiment includes a first contact member (a contact member) 102A, a second contact member (a contact member) 103A, receiving members 104A and 105A, and sheet members (biasing members) 106A and 107A, in place of the contact probes 39A and 40A of the position detection sensor 34A according to the first embodiment. The receiving members 104A and 105A support the contact members 102A and 103A. The sheet members 106A and 107A bias the contact members 102A and 103A.

The contact members 102A and 103A are formed of a conductive material such as stainless steel in a spherical shape. The first contact member 102A is arranged closer to the inner periphery side of the ring-shaped member 32A than the manipulation wire 35A in the through hole 46A. The first contact member 102A is formed so that a portion thereof projects to the inner periphery side of the ring-shaped member 32A when the first contact member 102A is arranged within the through hole 46A. On the other hand, the second contact member 103A is arranged closer to an outer periphery of the ring-shaped member 32A than the manipulation wire 35A in the through hole 46A. The second contact member 103A is formed so that a portion thereof projects to the outer periphery side of the support member 38A when the second contact member 103A is arranged within the through hole 46A.

The receiving member 104A is formed of a conductive material such as stainless steel in a plate shape having a concave portion 110A opened toward the axis C1. The receiving member 104A rotatably supports the first contact member 102A within the concave portion 110A. The receiving member 105A is formed of the same material as the receiving member 104A in a plate shape having a concave portion 111A opened toward to the axis C1. The receiving member 105A rotatably supports the second contact member 103A within the concave portion 111A.

A position T4 in which the second contact member 103A comes in contact with the conductive ring 36A or the insulating ring 37A is shifted to the distal end by a half of the length L relative to a position T3 in which the first contact member 102A comes in contact with the conductive ring 36A or the insulating ring 37A.

The sheet members 106A and 107A are formed of a material having elasticity such as rubber in a sheet shape. An edge portion of the sheet member 106A is attached to an edge portion of the through hole 46A of the support member 38A. A central part of the sheet member 106A biases the first contact member 102A to the axis C1 through the receiving member 104A. Similarly, an edge portion of the sheet member 107A is attached to the edge portion of the through hole 46A of the support member 38A. A central part of the sheet member 107A biases the second contact member 103A to the axis C1 through the receiving member 105A. Accordingly, a contact state of the first contact member 102A and the receiving member 104A and a contact state of the second contact member 103A and the receiving member 105A are held.

In the present embodiment, for example, ends of the wirings 51A and 56A are connected to the receiving members 104A and 105A, respectively.

According to the position detection sensor 101A having the above configuration according to the present embodiment, the outer diameter can be reduced.

The first contact member 102A is rotatably supported in the concave portion 110A of the receiving member 104A. Therefore, frictional resistance between each of the conductive ring 36A and the insulating ring 37A, and the first contact member 102A can be reduced when the manipulation wire 35A is pushed or retracted.

The contact members 102A and 103A are formed to be small, such that the position detection sensor 101A can be further miniaturized.

The through hole 46A may be sealed with the sheet members 106A and 107A.

In the present embodiment, the position detection sensor 101A may not include the receiving member 104A. In this case, the wiring 51A is connected to the first contact member 102A. The first contact member 102A slides on the outer periphery of the conductive ring 36A and the insulating ring 37A.

The sheet members 106A and 107A may be integrally formed of a thermal contraction tube or the like.

(Third Embodiment)

A third embodiment of the present invention is described with reference to FIGS. 20 to 24. In the present embodiment, the same portions in the present embodiment as those in the above embodiments are denoted with the same reference signs and a description thereof is omitted here, and only differences are described.

Figure 20:
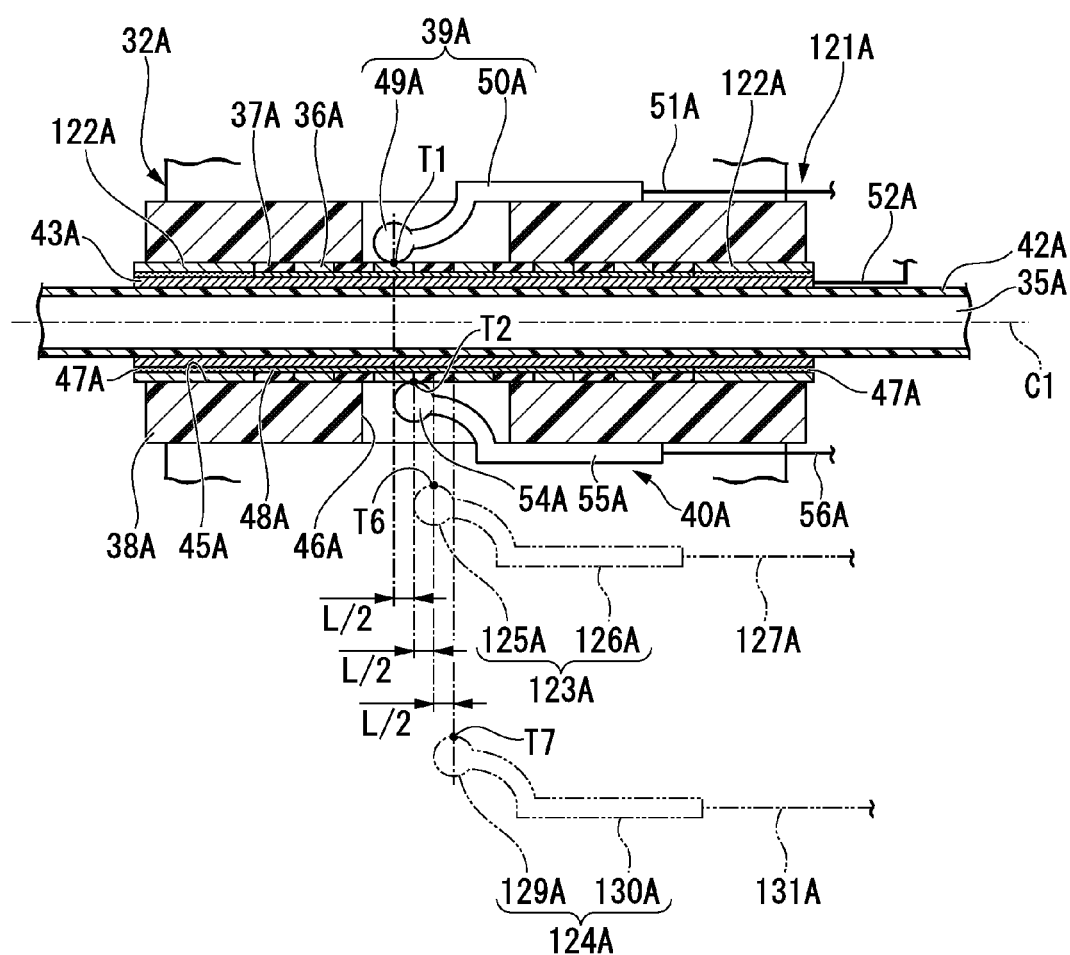
FIG. 20 is a lateral cross-sectional view of a position detection sensor according to a third embodiment of the present invention.

A position detection sensor 121A according to the present embodiment includes a second conductive ring (a second conductive portion) 122A, a third contact probe 123A, and a fourth contact probe 124A, in addition to each configuration of the position detection sensor 34A according to the first embodiment, as illustrated in FIG. 20. A third contact member 125A of the third contact probe 123A (described later) and a fourth contact member 129A of the fourth contact probe 124A (described later) come in contact with the outer peripheries of the conductive ring 36A and the insulating ring 37A in a point form, similar to the contact members 49A and 54A. However, in FIG. 20, positions other than the direction of the axis C1 in the third contact probe 123A and the fourth contact probe 124A are shown to be shifted, for convenience of explanation.

The second conductive ring 122A is formed in an annular shape whose outer and inner diameters are equal to those of the conductive ring 36A. The width of the second conductive ring 122A is set to twice the width of the conductive ring 36A. In the present embodiment, the second conductive rings 122A are used in place of the rings 36A and 37A located at both ends. The second conductive rings 122A are arranged such that the rings 36A and 37A located in the intermediate part are interposed between the second conductive rings 122A in the direction of the axis C1. Each second conductive ring 122A is fixed to the connecting pipe 43A by the above-described adhesive 47A.

The third contact probe 123A and the fourth contact probe 124A have the same configuration as the first contact probe 39A. That is, the third contact probe 123A includes a third contact member (a contact member) 125A and a plate spring (a biasing member) 126A. The fourth contact probe 124A includes a fourth contact member (a contact member) 129A and a plate spring (a biasing member) 130A.

In the present embodiment, each of the first contact member 49A of the first contact probe 39A, the second contact member 54A of the second contact probe 40A, the third contact member 125A of the third contact probe 123A, and the fourth contact member 129A of the fourth contact probe 124A is configured to be able to come in contact with the outer peripheries of the conductive ring 36A, the insulating ring 37A, and the second conductive ring 122A (hereinafter referred to as "the conductive ring 36A or the like") in a point form.

As described above, the position T2 in which the second contact member 54A comes in contact with the conductive ring 36A or the like is shifted to the proximal end by a half of the length L relative to the position T1 in which the first contact member 49A comes in contact with the conductive ring 36A or the like. A position T6 in which the third contact member 125A comes in contact with the conductive ring 36A or the like is shifted to the proximal end by a half of the length L relative to the position T2 in which the second contact member 54A comes in contact with the conductive ring 36A or the like. A position T7 in which the fourth contact member 129A comes in contact with the conductive ring 36A or the like is shifted to the proximal end by a half of the length L relative to the position T6 in which the third contact member 125A comes in contact with the conductive ring 36A or the like.

A third detector and a fourth detector (not illustrated) having the same configuration as the first detector 83 are included in the control device 80.

A wiring 127A connected to the plate spring 126A of the third contact probe 123A and the wiring 52A connected to the connecting pipe 43A are connected to the third detector. A wiring 131A connected to the plate spring 130A of the fourth contact probe 124A and the wiring 52A connected to the connecting pipe 43A are connected to the fourth detector.

A signal indicating the conduction state or the blocking state detected by each of the first detectors 83 and 84, the second detectors 85 and 86, the third detector, and the fourth detector is output to the slave controller 87.

Figure 21:
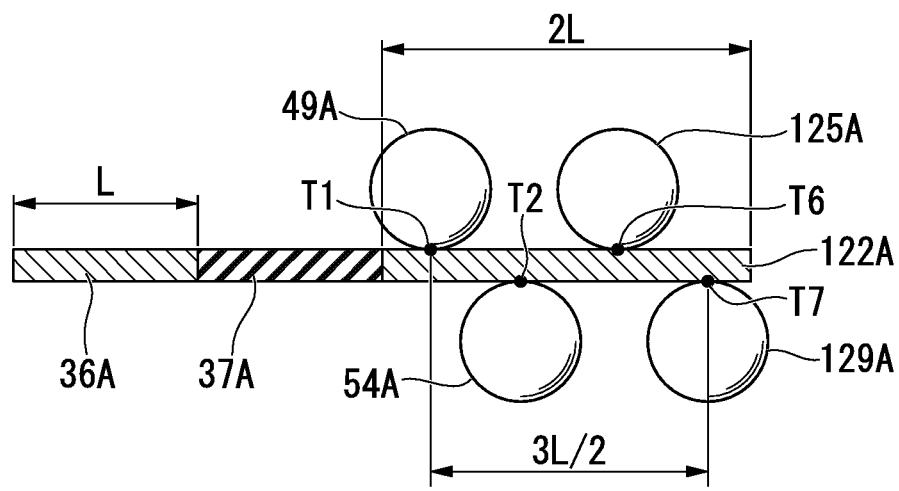
FIG. 21 is a schematic view illustrating a relation of positions of a conductive ring, a second conductive ring, and an insulating ring with respect to a contact member of the position detection sensor.

A distance between the position T1 and the position T7 in the direction of the axis C1 is a value from an expression of 3L/2, as illustrated in FIG. 21. Accordingly, when the positions T1, T2, T6, and T7 are on the second conductive ring 122A together, the contact members 49A, 54A, 125A, and 129A are all in the conduction state. The positions T1, T2, T6, and T7 together on the second conductive ring 122A located at the end among the rings 36A, 37A, and 122A (a limit being ON) is determined. In this case, the bending portion 23A may be controlled not to be bent.

Figure 22:
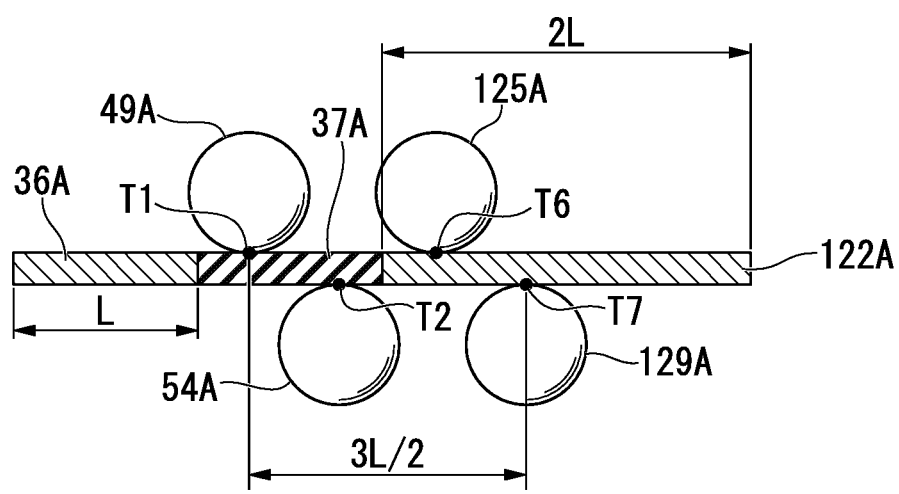
FIG. 22 is a schematic view illustrating a relation of positions of the conductive ring, the second conductive ring, and the insulating ring with respect to the contact member of the position detection sensor.

On the other hand, when at least one of the positions T1, T2, T6, and T7 is not on the second conductive ring 122A, at least one of the contact members 49A, 54A, 125A, and 129A enters the blocking state, as illustrated in FIG. 22.

Figure 23:
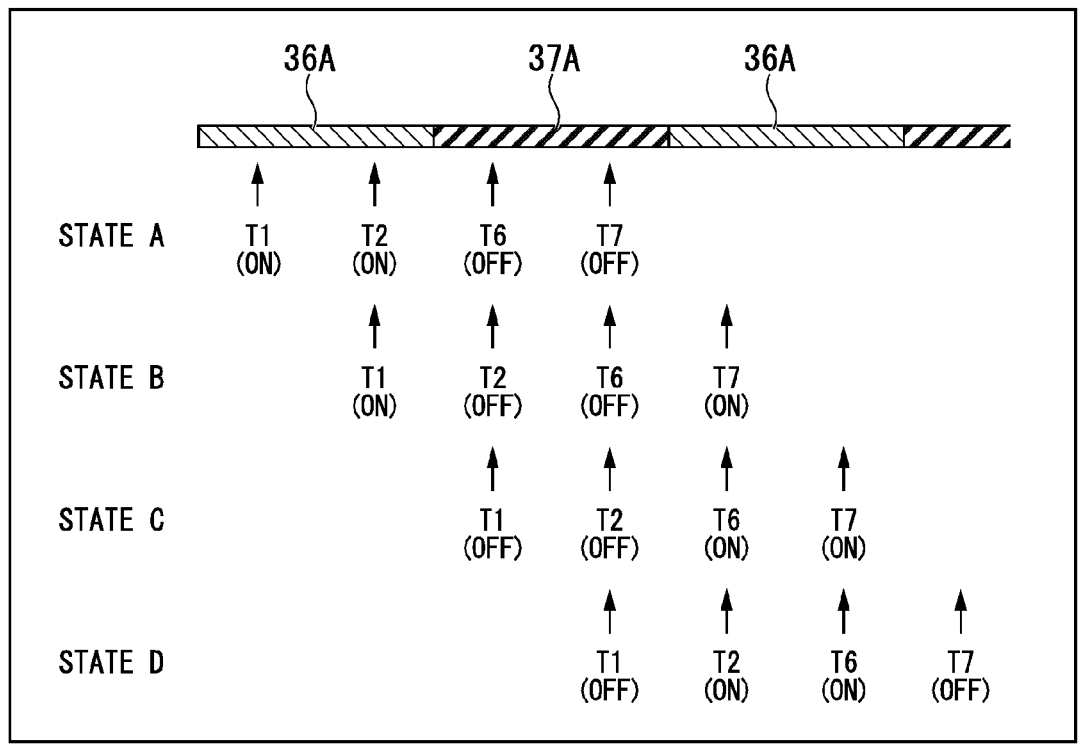
FIG. 23 is a schematic view illustrating a position in which the contact member comes in contact with the conductive ring and the insulating ring of the position detection sensor.

More specifically, a case in which the manipulation wire 35A is pushed at a constant speed from the state A illustrated in FIG. 23 is described. As illustrated in FIG. 23, positions of the rings 36A and 37A of the manipulation wire 35A are fixed and the positions T1, T2, T6, and T7 are retracted.

In the state A, a switch corresponding to each of the positions T1 and T2 becomes ON, and a switch corresponding to each of the positions T6 and T7 becomes OFF. As the manipulation wire 35A is pushed from the state A, the switch corresponding to the position T2 becomes OFF and the switch corresponding to the position T7 becomes ON in the state B. In the state C, the switch corresponding to the position T1 becomes ON, and the switch corresponding to the position T6 becomes ON. In the state D, the switch corresponding to the position T2 becomes ON, and the switch corresponding to the position T7 becomes OFF. In the state A, the switch corresponding to the position T1 becomes ON, and the switch corresponding to the position T6 becomes OFF.

Figure 24:
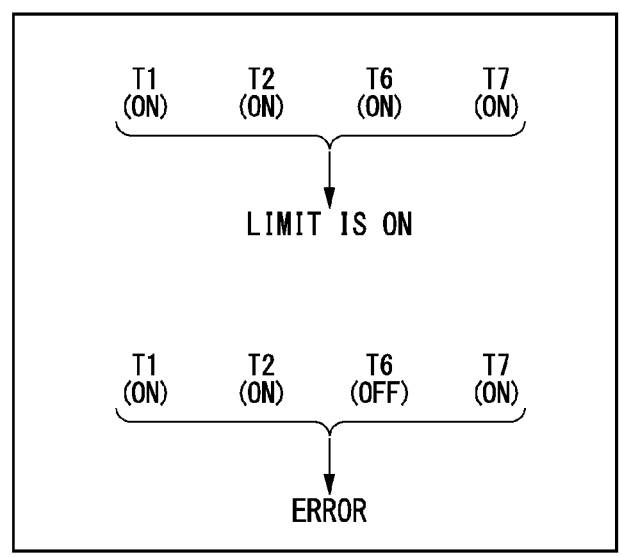
FIG. 24 is a diagram illustrating an ON/OFF state of a switch corresponding to each position of the position detection sensor.

In the state illustrated in FIG. 21, all the switches corresponding to the positions T1, T2, T6, and T7 become ON, and the limit is determined to be ON, as illustrated in FIG. 24.

However, only the switch corresponding to the position T2 or the position T6 among the switches corresponding to the position T1, T2, T6, and T7 does not become OFF, as illustrated in FIG. 24. In this case, it is determined that there is an abnormality (an error) in the position detection sensor.

According to the position detection sensor 121A having the above configuration according to the present embodiment, the outer diameter can be reduced.

A state in which the contact members 49A, 54A, 125A, and 129A all come in contact with the second conductive ring 122A can be detected.

In the present embodiment, the second conductive ring 122A may be configured by arranging the plurality of conductive rings 36A in the direction of the axis C1.

In the present embodiment, the second conductive rings 122A is arranged such that the rings 36A and 37A located in the intermediate part are interposed between the second conductive rings 122A in the direction of the axis C1. However, the second conductive ring 122A may be arranged between the rings 36A and 37A constituting the rings 36A and 37A located in the intermediate part.

The insulating member having the same shape as the second conductive ring 122A may be used in place of the second conductive ring 122A. In this case, when the positions T1, T2, T6, and T7 are on the member together, all the contact members 49A, 54A, 125A, and 129A enter the blocking state. Accordingly, a state in which the contact members 49A, 54A, 125A, and 129A all come in contact with the member can be detected.

(Fourth Embodiment)

A fourth embodiment of the present invention is described with reference to FIG. 25. In the present embodiment, the same portions as those in the above embodiments are denoted with the same reference signs and a description thereof is omitted here, and only differences are described.

Figure 25:
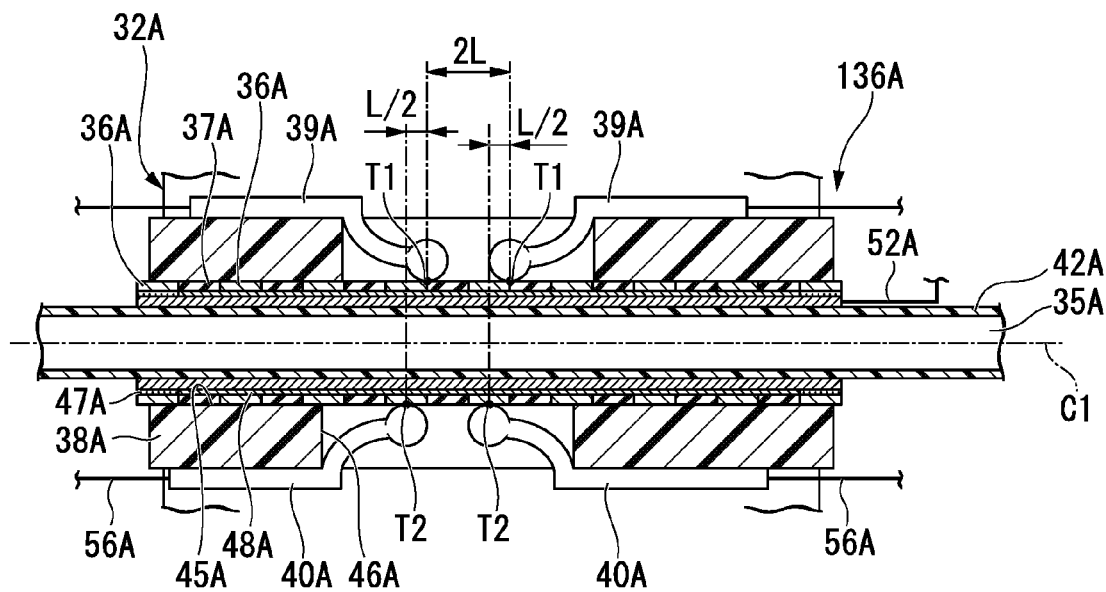
FIG. 25 is a lateral cross-sectional view of a position detection sensor according to a fourth embodiment of the present invention.

A position detection sensor 136A according to the present embodiment includes two sets of the first contact probe 39A and the second contact probe 40A, as illustrated in FIG. 25. A position T1 in which a first contact member 49A of the one first contact probe 39A comes in contact and a position T1 in which a first contact member 49A of the other first contact probe 39A comes in contact are shifted by twice of the length L in the direction of the axis C1. The second contact probes 40A are similarly set.

In the present embodiment, the control device 80 includes two sets of the first detector 83 and the second detector 85.

According to the position detection sensor 136A having the above configuration according to the present embodiment, the conduction states or the blocking states of two of the first contact probes 39A are equal to each other. The same applies to two of the second contact probes 40A. Accordingly, it is possible to increase reliability of signals of the contact probes 39A and 40A. Therefore, it is possible to more reliably detect the position of the manipulation wire 35A and to improve safety of the position detection sensor 136A.

The number of sets of the contact probes 39A and 40A included in the position detection sensor 136A is not limited and three or more sets may be included.

(Fifth Embodiment)

A fifth embodiment of the present invention is described with reference to FIG. 26. In the present embodiment, the same portions as those in the above embodiments are denoted with the same reference signs and a description thereof is omitted here, and only differences are described.

Figure 26:
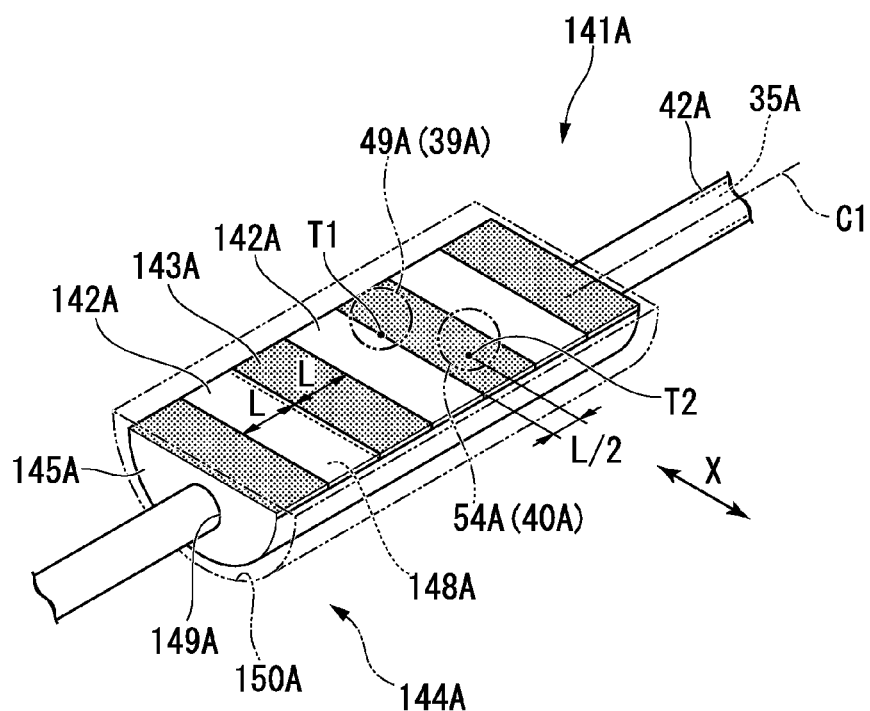
FIG. 26 is a perspective view of a major part of a position detection sensor according to a fifth embodiment of the present invention.

As illustrated in FIG. 26, a position detection sensor 141A according to the present embodiment includes a conductive plate (a conductive portion) 142A, an insulating plate (an insulating portion) 143A, a support member 144A, and a holding member 145A, in place of the conductive ring 36A, the insulating ring 37A, the support member 38A, and the connecting pipe 43A of the position detection sensor 34A according to the first embodiment.

Hereinafter, the holding member 145A is described first. The holding member 145A is formed in a tubular shape and includes a holding surface 148A parallel to the axis C1 on an outer surface thereof. More specifically, an outer form of the holding member 145A is formed in a D-shape when viewed in the direction of the axis C1. It is preferable that the holding member 145A is formed of a conductive material.

The manipulation wire 35A covered with the covering material 42A is inserted into a through hole 149A formed in the holding member 145A in the direction of the axis C1. The holding member 145A is fixed to the covering material 42A with adhesion or caulking.

The conductive plates 142A and the insulating plates 143A having a flat shape described above are alternately arranged without a gap in the direction of the axis C1 on the holding surface 148A. The lengths of the conductive plates 142A and the insulating plates 143A in the direction of the axis C1 are set to the above-described length L. The conductive plates 142A and the insulating plates 143A are fixed to the holding surface 148A using a conductive adhesive (not illustrated) or the like.

In the present embodiment, the first contact member 49A of the first contact probe 39A and the second contact member 54A of the second contact probe 40A are arranged in parallel to the holding surface 148A and in a position shifted in an orthogonal direction X orthogonal to the direction of the axis C1. A position T2 in which the second contact member 54A comes in contact with an outer surface of the conductive plate 142A or the insulating plate 143A is shifted to the proximal end by a half of the length L relative to a position T1 in which the first contact member 49A comes in contact with the outer surface of the conductive plate 142A or the insulating plate 143A.

The support member 144A differs from the support member 38A according to the first embodiment in only a shape of a through hole 150A. The through hole 150A is formed in a D shape which is slightly larger than an outer shape of the holding member 145A when viewed in the direction of the axis C1. That is, the holding member 145A inserted into the through hole 150A of the support member 144A can be advanced and retracted in the direction of the axis C1 with respect to the support member 144A, but rotation in the circumferential direction of the manipulation wire 35A is prevented.

With the position detection sensor 141A having the above configuration, it is possible to achieve the same effect as the position detection sensor 34A according to the above embodiments.

In the present embodiment, a plurality of conductive plates 142A and insulating plates 143A are arranged on the holding surface 148A. However, at least one of each of the conductive plate 142A and the insulating plate 143A may be arranged on the holding surface 148A.

In the first embodiment, and the third embodiment to the fifth embodiment, the contact member is formed in a spherical shape. However, the shape of the contact member is not particularly limited as long as the contact member can come in contact with the outer periphery of the conductive ring 36A or the like in the direction of the axis C1 in a point form. Specifically, the contact member may be formed in a dome shape, a columnar shape, or the like in which a portion thereof near the axis C1 is formed in a curved surface which is convex towards the conductive ring 36A.

In the first embodiment, the position in which the second contact member comes in contact is shifted to the proximal end by a half of the length L relative to the position with which the first contact member comes in contact. However, in the first embodiment to the fifth embodiment, the shift of the position in the direction of the axis C1 may be greater than 0 and smaller than the length L, and the direction of the shift may be directed toward the proximal end or the distal end. With this configuration, it is also possible to achieve the same effects as the embodiments described above.

The lengths of the conductive ring 36A and the insulating ring 37A in the direction of the axis C1 of the manipulation wire 35A are set to be substantially equal to each other. Hereinafter, the lengths of the conductive ring 36A and the insulating ring 37A are described in detail.

In the above embodiments, the first contact member 49A can come in contact with the outer peripheries of the conductive ring 36A and the insulating ring 37A in the direction of the axis C1 in a point form. Here, a length by which the first contact member 49A comes in contact with the outer peripheries of the conductive ring 36A and the insulating ring 37A in the direction of the axis C1 is defined as $L_3$.

Figure 27:
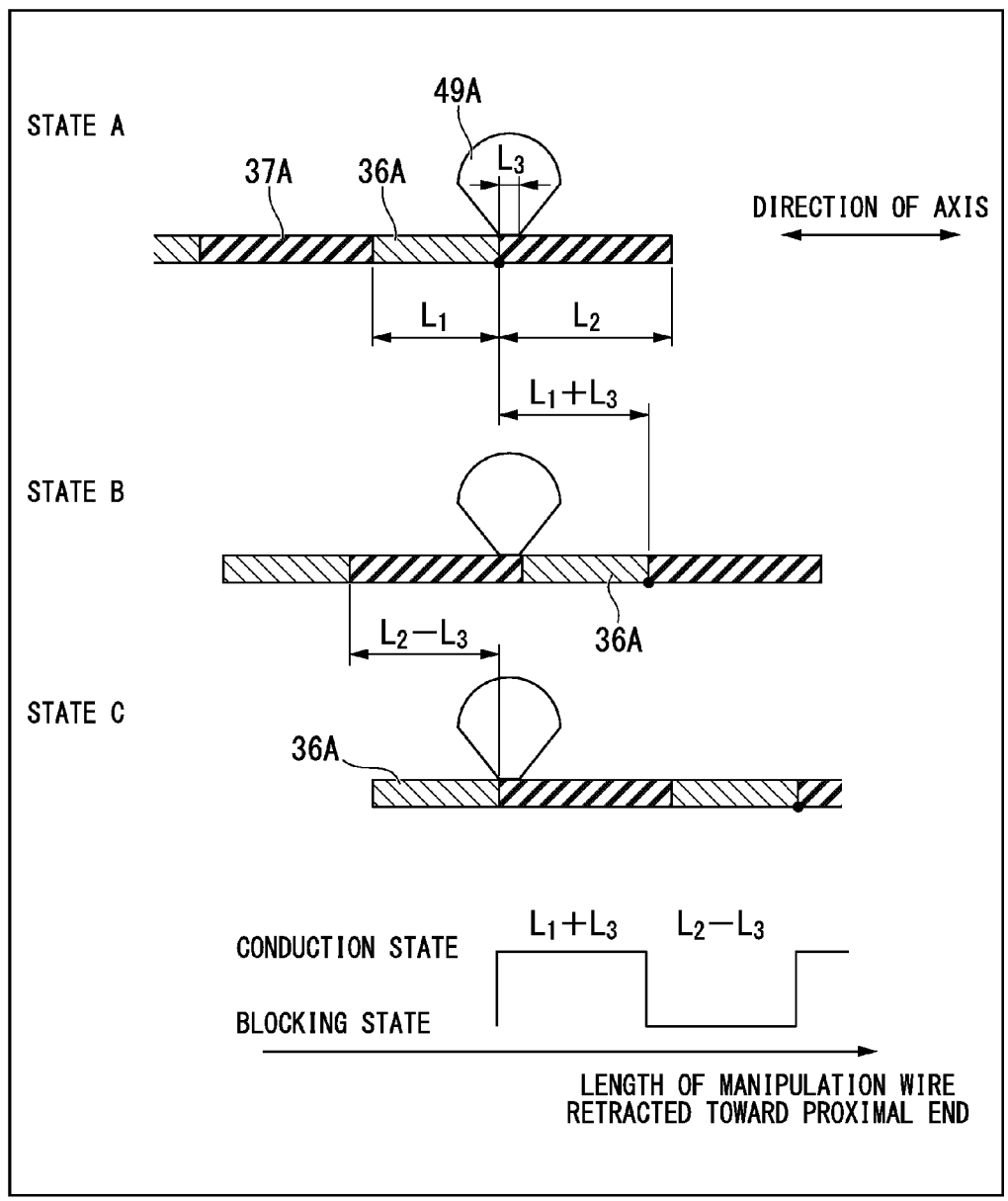
FIG. 27 is a diagram illustrating a contact state between a conductive ring and an insulating ring, and a first contact member.

When a case in which the manipulation wire 35A is retracted is considered, the first contact member 49A comes in contact with the conductive ring 36A and enters the conduction state from the state A in which the first contact member 49A comes in contact with the proximal end portion of the conductive ring 36A illustrated in FIG. 27. Here, the length of the conductive ring 36A in the direction of the axis C1 is defined as $L_1$, and the length of the insulating ring 37A in the direction of the axis C1 is defined as $L_2$. The conduction state continues while the manipulation wire 35A is retracted by a value of an expression of $L_1+L_3$ from the state A to the state B in which the first contact member 49A comes in contact with the distal end portion of the conductive ring 36A. When the manipulation wire 35A is further retracted from the state B, the state becomes the blocking state until the first contact member 49A comes in contact with the proximal end portion of the conductive ring 36A arranged on the distal side of the conductive ring 36A with which the first contact member 49A has been in contact so far, as in the state C. The length by which the manipulation wire 35A is retracted from the state B to the state C has a value of an expression of $L_2-L_3$.

If the length by which the manipulation wire 35A is retracted in the conduction state from the state A to state B is equal to the length by which the manipulation wire 35A is retracted in the blocking state from the state B to state C, Expression (1) is derived. Accordingly, a relation between the length $L_1$ of the conductive ring 36A and the length $L_2$ of the insulating ring 37A is as shown in Expression (2).

$$L_1+L_3=L_2-L_3, \quad (1)$$

$$L_1+2L_3=L_2 \quad (2)$$

That is, the lengths of the rings 36A and 37A are set to satisfy Expression (2), such that lengths by which the conduction state and the blocking state are switched become equal when the manipulation wire 35A is retracted or pushed. Through this configuration, it is possible to easily perform the calculation of the position of the manipulation wire 35A in the direction of the axis C1.

The lengths of the conductive ring 36A and the insulating ring 37A in the direction of the axis C1 are set substantially equal to each other. However, the lengths of the conductive ring 36A and the insulating ring 37A in the direction of the axis C1 may be set to differ from each other. If the lengths are stored in a memory of the first detector 83 of the control device 80, the position of the manipulation wire 35A in the direction of the axis C1 can be corrected.

The conductive ring 36A, the insulating ring 37A, and the connecting pipe 43A of the position detection sensor may be manufactured in the following procedure. A groove is formed over the entire circumference in an outer periphery of a conductive pipe material. The groove may be formed through laser processing or mechanical processing such as cutting. A plurality of grooves are formed to be spaced from each other in a longitudinal direction of the pipe material. A silica-based solution is applied within this groove and dried. An insulating portion is formed in the groove by polishing an outer periphery of the pipe material after drying. The outer periphery of the pipe material adjacent to the insulating portion in a longitudinal direction becomes a conductive portion.

The procedures described above include the following other procedures. In a cross section including the axis of the pipe material formed of aluminum, concavity and convexity in a wave form is formed in the outer periphery. An alumite layer is formed over an entire surface in the outer periphery. A portion formed on a convex portion in the formed alumite layer of the outer periphery is removed through abrasion or the like, such that a portion of aluminum and a portion of alumite are alternately formed in the longitudinal direction on the outer periphery.

(Sixth Embodiment)

A sixth embodiment of the present invention is described with reference to FIGS. 28 to 32. In the present embodiment, the same portions as those in the above embodiments are denoted with the same reference signs and a description thereof is omitted here, and only differences are described.

Figure 28:
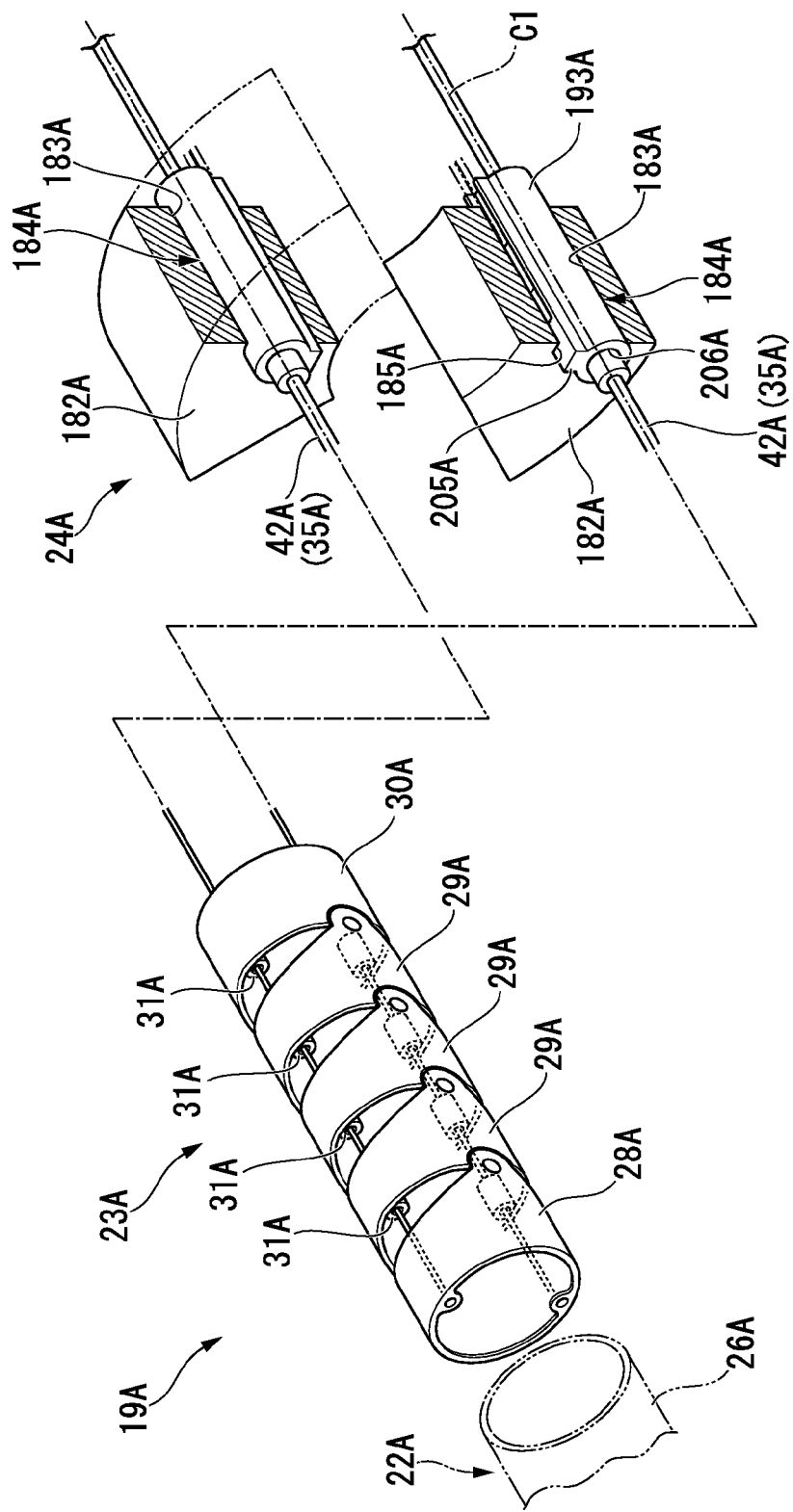
FIG. 28 is a partially cutaway perspective view illustrating an internal configuration of a manipulator according to a sixth embodiment of the present invention.

In the present embodiment, a bending amount detector 24A includes a pair of attachment members 182A, as illustrated in FIG. 28. A position detection sensor 184A according to the present embodiment is attached to each of through holes 183A formed in the pair of attachment members 182A in a state in which the position detection sensor 184A is inserted into each of the through holes 183A. The through hole 183A is formed in a cylindrical shape, and a concave portion 185A recessed from an inner periphery of the through hole 183A to the outside in a radial direction is formed. It is preferable that the attachment member 182A is formed of a material having insulation properties such as a resin or ceramics. While the example in which the manipulator 19A includes the two position detection sensors 184A and the two attachment members 182A is described in order to make an explanation easier to understand, it is preferable that the attachment member is formed in an annular shape since four position detection sensors 184A are included in a real use form.

The pair of attachment members 182A are arranged to face each other. The pair of attachment members 182A are fixed to the above-described proximal ring 30A through a fixing member which is not illustrated. That is, the distal ring 28A and the bending piece 29A are pivotably supported by each attachment member 182A.

Figure 29:
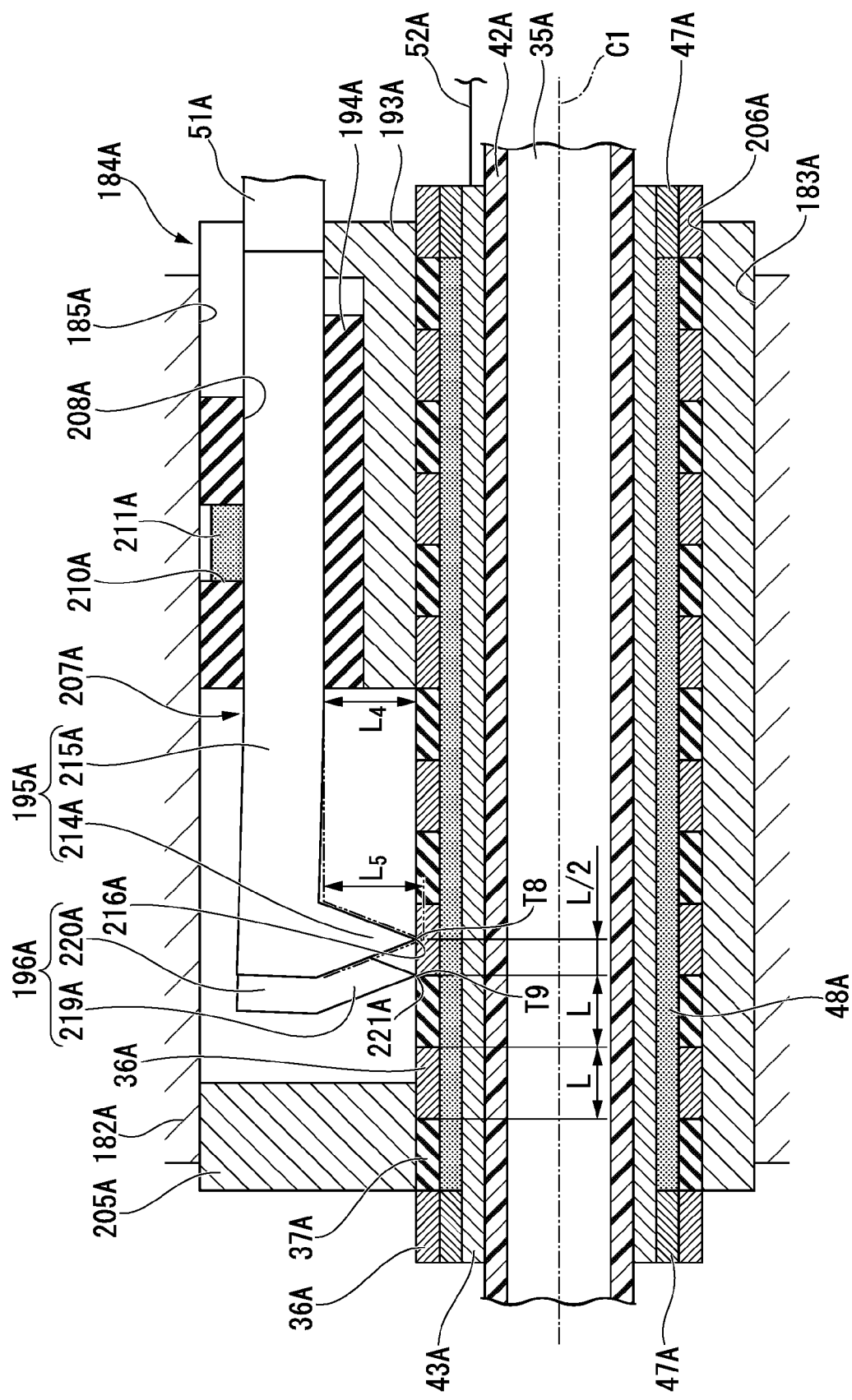
FIG. 29 is a lateral cross-sectional view of a position detection sensor of the manipulator.
Figure 30:
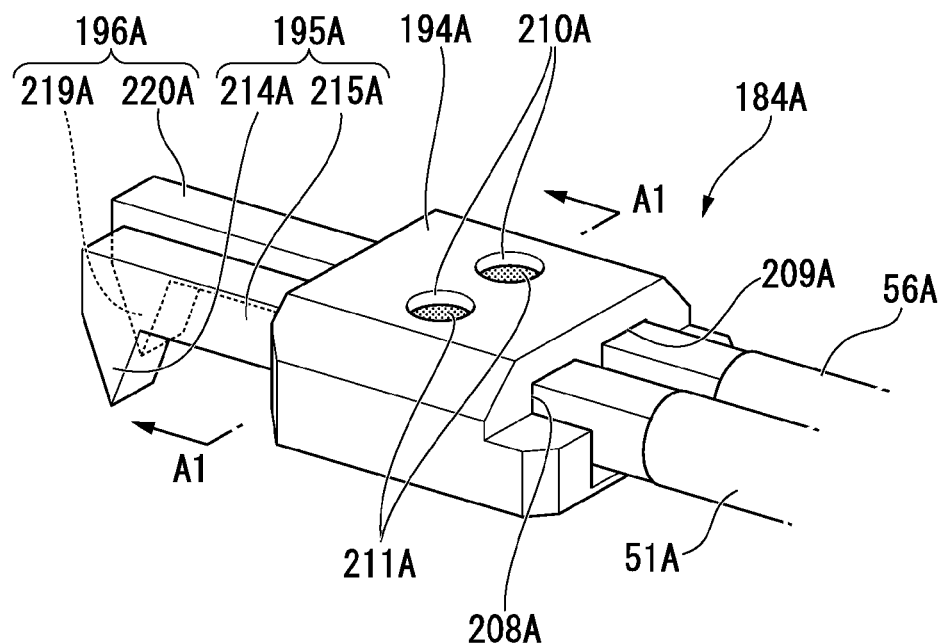
FIG. 30 is a perspective view of a major part of the position detection sensor.

The position detection sensor 184A according to the present embodiment includes a support member 193A, a first contact probe 195A, and a second contact probe 196A, in place of the support member 38A, the first contact probe 39A, and the second contact probe 40A of the position detection sensor 34A according to the first embodiment, as illustrated in FIGS. 29 and 30. The support member 193A is provided to be able to be advanced or retracted in the direction of the axis C1 of the manipulation wire 35A with respect to the conductive ring 36A and the insulating ring 37A. The first contact probe 195A and the second contact probe 196A are attached to the support member 193A through a holding member 194A.

The support member 193A is formed in a cylindrical shape, as illustrated in FIGS. 28 and 29. An outer diameter of the support member 193A is slightly smaller than an inner diameter of the through hole 183A of the attachment member 182A. A convex portion 205A which projects outward in a radial direction is formed in an outer periphery of the support member 193A. A through hole 206A and an internal space 207A are formed in the support member 193A. The through hole 206A extends in the direction of the axis C1. The internal space 207A communicates from an intermediate part of the through hole 206A in the direction of the axis C1 to a distal end of the convex portion 205A in a projecting direction. It is preferable that the support member 193A and the holding member 194A are formed of the same material as the attachment member 182A.

The support member 193A having the above configuration is fixed with an adhesive (not illustrated) in a state in which the support member 193A is inserted into the through hole 183A of the attachment member 182A. Here, the convex portion 205A of the support member 193A is engaged with the concave portion 185A of the through hole 183A, so that the support member 193A can be reliably fixed to the attachment member 182A. The manipulation wire 35A in which the plurality of conductive rings 36A and insulating rings 37A are provided is inserted into the through hole 206A of the support member 193A so as to be able to be advanced or retracted in the direction of the axis C1.

Figure 31:
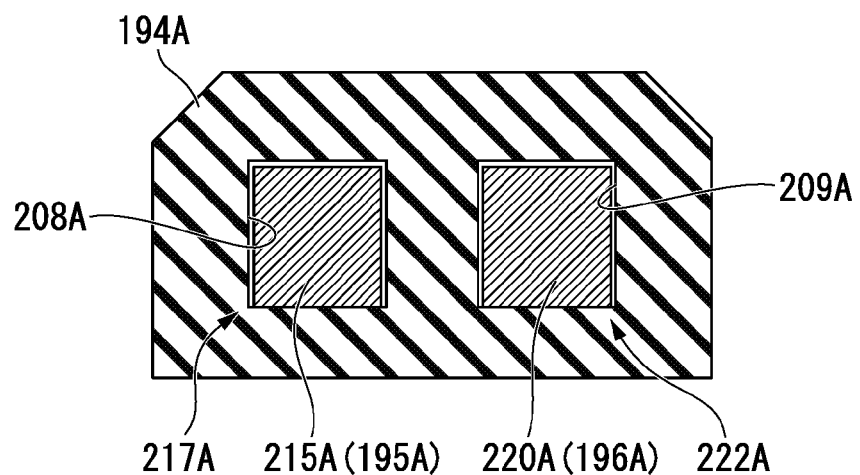
FIG. 31 is a cross-sectional view taken along a cutting line A1-A1 in FIG. 30.

In the present embodiment, the holding member 194A is formed in a rectangular parallelepiped shape, as illustrated in FIGS. 29 to 31. A first holding hole 208A and a second holding hole 209A extending in the direction of the axis C1 are formed in the holding member 194A. In the present embodiment, a cross-sectional shape of the holding holes 208A and 209A in a plane orthogonal to the axis C1 is formed in a rectangular shape.

Communicating holes 210A which communicate from the outside to the first holding hole 208A and from the outside to the second holding hole 209A, respectively, are formed in the holding member 194A. Contact probes 195A and 196A inserted into the holding holes 208A and 209A, respectively, are fixed to the holding member 194A using an adhesive (a fixing portion) 211A injected into the holding holes 208A and 209A through the communicating holes 210A. The holding member 194A is arranged within the internal space 207A and fixed to the support member 193A.

The first contact probe 195A includes a first contact member (a contact member) 214A and a first plate spring (a first biasing member) 215A. The first contact member 214A is arranged on an outer side in the radial direction of the conductive ring 36A and the insulating ring 37A. The first contact member 214A is attached to a distal end portion of the first plate spring 215A. In the first contact member 214A, a sharp distal end 216A which is on a side of the rings 36A and 37A is formed. The distal end 216A has a shape which becomes a triangle in a side view. The first plate spring 215A is formed in a flat shape extending in the direction of the axis C1. A cross-sectional shape of the first plate spring 215A in a plane orthogonal to the axis C1 is formed in a rectangular shape. The cross-sectional shape of the first plate spring 215A is slightly smaller than the cross-sectional shape of the first holding hole 208A described above. The first contact member 214A and the first plate spring 215A are integrally formed of a material having conductivity and elasticity such as stainless steel.

When the first plate spring 215A of the first contact probe 195A is inserted into the first holding hole 208A of the holding member 194A, the holding member 194A holds the first plate spring 215A in the first holding hole 208A, and prevents the first plate spring 215A from rotating about its own longitudinal direction in the first holding hole 208A. This is because a corner portion of the first plate spring 215A having the cross-sectional shape formed in a rectangular shape is engaged with an inner surface of the first holding hole 208A. Thus, a rotation prevention portion 217A is configured of the first holding hole 208A of the holding member 194A and the first plate spring 215A (see FIG. 31).

A distance $L_4$ between the outer peripheries of the rings 36A and 37A and the first plate spring 215A when the first plate spring 215A is inserted into the first holding hole 208A is shorter than a length $L_5$ of the first contact member 214A projecting from the first plate spring 215A to the outer peripheries of the rings 36A and 37A, as illustrated in FIG. 29. The first plate spring 215A inserted into the first holding hole 208A is fixed to the holding member 194A by the adhesive 211A. That is, the first contact probe 195A is attached to the support member 193A through the holding member 194A.

The distance $L_4$ and the length $L_5$ are set as described above, so that the first contact member 214A is configured such that the distal end 216A reliably comes in contact with the outer peripheries of the rings 36A and 37A by an biasing force toward the outer peripheries of the rings 36A and 37A generated by the first plate spring 215A. In this case, the outer peripheries of the rings 36A and 37A and the distal end 216A of the first contact member 214A can come in contact with each other in a point form.

The second contact probe 196A is configured like the first contact probe 195A. The second contact probe 196A includes a second contact member (a contact member) 219A and a second plate spring (a second biasing member) 220A. The second contact member 219A is arranged on an outer side in the radial direction of the conductive ring 36A and the insulating ring 37A. The second contact member 219A is attached to the distal end portion of the second plate spring 220A.

For the second contact probe 196A, when the second plate spring 220A of the second contact probe 196A is inserted into the second holding hole 209A of the holding member 194A, the holding member 194A holds the second plate spring 220A in the second holding hole 209A, and prevents the second plate spring 220A from rotating about its own longitudinal direction in the second holding hole 209A. Thus, a rotation prevention portion 222A is configured of the second holding hole 209A of the holding member 194A and the second plate spring 220A (see FIG. 31). The second plate spring 220A inserted into the second holding hole 209A is fixed to the holding member 194A using the adhesive 211A. That is, the second contact probe 196A is attached to the support member 193A through the holding member 194A.

The second contact member 219A is configured such that a distal end 221A of the second contact member 219A reliably comes in contact with the outer peripheries of the rings 36A and 37A by a biasing force toward the outer peripheries of the rings 36A and 37A generated by the second plate spring 220A, as illustrated in FIG. 29.

The holding member 194A described above can adjust a position of the second plate spring 220A with respect to the first plate spring 215A in the direction of the axis C1 by moving the plate springs 215A and 220A in the direction of the axis C1 in the holding holes 208A and 209A before the plate springs 215A and 220A are fixed using the adhesive 211A. A position T9 in which the distal end 221A of the second contact member 219A comes in contact with the outer peripheries of the rings 36A and 37A is shifted to the distal end by a half of the length L (a predetermined distance) relative to a position T8 in which the distal end 216A of the first contact member 214A comes in contact with the outer peripheries of the rings 36A and 37A.

Thus, the first contact probe 195A and the second contact probe 196A are attached to the support member 193A together with the holding member 194A.

In the present embodiment, as illustrated in FIG. 30, the ends of the wirings 51A and 56A are connected to the first plate spring 215A and the second plate spring 220A, respectively.

The position detection sensor 184A of the manipulator system 1 having the above configuration adjusts, for example, a distance between the distal end 216A of the first contact member 214A and the distal end 221A of the second contact member 219A in the direction of the axis C1, as is described below.

The contact probes 195A and 196A are moved in the direction of the axis C1 using tweezers or the like in the holding holes 208A and 209A of the holding member 194A while observing the position detection sensor 184A not fixed by the adhesive 211A through a stereomicroscope or the like. The rotation prevention portions 217A and 222A are included in the position detection sensor 184A. Therefore, the first plate spring 215A does not rotate about its own longitudinal direction in the first holding hole 208A, and the second plate spring 220A does not rotate about its own longitudinal direction in the second holding hole 209A. Accordingly, directions of the contact members 214A and 219A about their own longitudinal directions are not shifted.

The distal end 221A of the second contact member 219A is adjusted to be shifted to the distal end by a half of the length L relative to the distal end 216A of the first contact member 214A. The adhesive 211A before becoming solidified is dropped over the each communicating hole 210A to solidify the adhesive 211A. Accordingly, the contact probes 195A and 196A are fixed in the holding holes 208A and 209A.

In the above-described procedure, the distance between the distal end 216A of the first contact member 214A and the distal end 221A of the second contact member 219A of the position detection sensor 184A is adjusted.

The distance between the distal ends 216A and 221A may be adjusted by moving the second contact probe 196A in the direction of the axis C1 with respect to the holding member 194A in a state in which the first contact probe 195A is fixed to the holding member 194A in advance.

With the position detection sensor 184A having the above configuration according to the present embodiment, it is possible to achieve the same effects as those in the position detection sensor 34A according to the first embodiment above and to reduce the outer diameter of the position detection sensor 184A.

In the present embodiment, the holding member 194A adjusts the position of the second plate spring 220A with respect to the first plate spring 215A in the direction of the axis C1, and then the plate springs 215A and 220A are fixed to the holding member 194A by the adhesive 211A. Through this configuration, the distance between the distal ends 221A and 216A in the direction of the axis C1 can be easily adjusted to fix the plate springs 215A and 220A. Accordingly, a period in which the switch S1 is ON and a period in which the switch S1 is OFF when the manipulation wire 35A is pushed with respect to the support member 193A at a constant speed can be set to a one-to-one correspondence in length, and measurement accuracy of the position detection sensor 184A can be improved.

The position detection sensor 184A includes the rotation prevention portion 217A. Accordingly, it is possible to prevent a direction of the first contact member 214A from being shifted with respect to the holding member 194A when the first plate spring 215A is moved in the direction of the axis C1 in the first holding hole 208A of the holding member 194A when the first plate spring 215A is not fixed by the adhesive 211A. Therefore, the direction of the first contact member 214A is stable, and measurement accuracy of the position detection sensor 34A can be improved.

Figure 32:
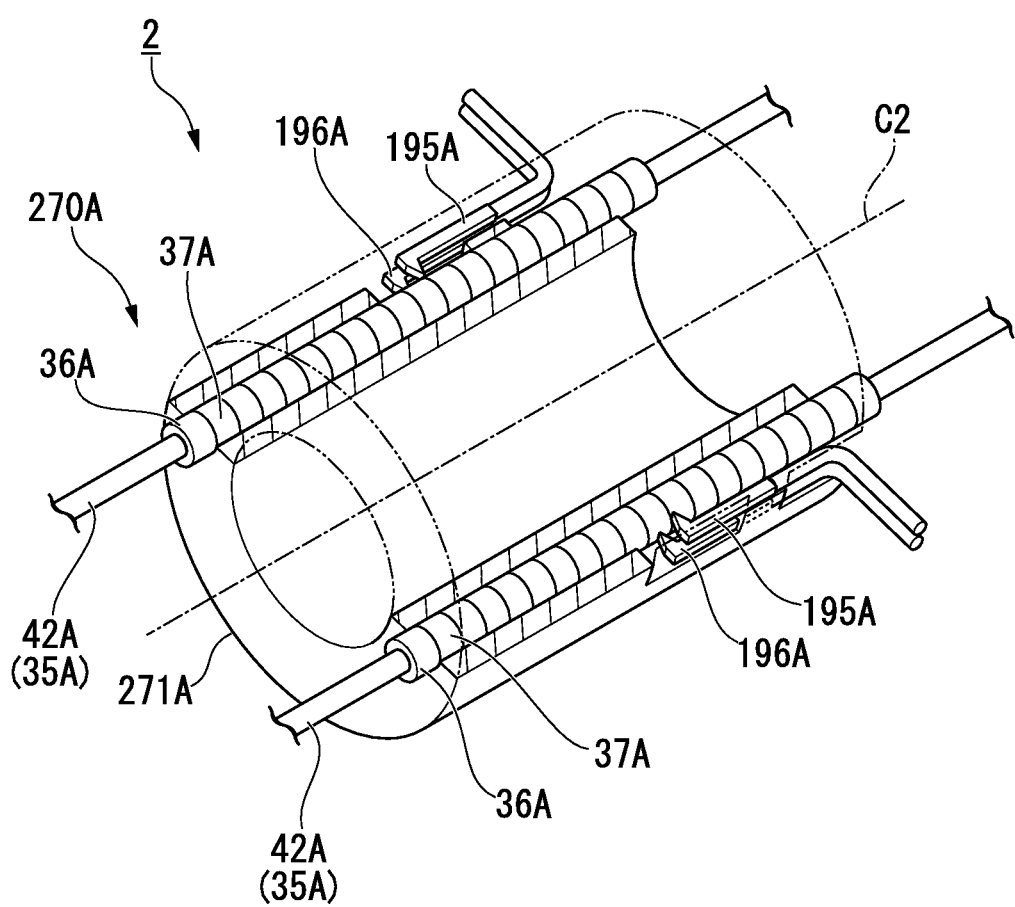
FIG. 32 is a partially cutaway perspective view of a position detection sensor in a modified example of the position detection sensor according to the sixth embodiment of the present invention.

In the present embodiment, the support member 271A may be formed in an annular shape, like the position detection sensor 270A illustrated in FIG. 32. In this example, the attachment member 182A and the holding member 194A described above are not included in the manipulator system 2, and when a pair of contact probes 195A and 196A form one set, two sets are directly attached to the support member 271A. The manipulation wires 35A and the sets of contact probes 195A and 196A are attached to the support member 271A to face each other with an axis C2 of the support member 271A interposed therebetween.

As the position detection sensor 270A is configured as described above, a plurality of sets of contact probes 195A and 196A can be integrally handled.

(Seventh Embodiment)

A seventh embodiment of the present invention is described with reference to FIGS. 33 to 35. In the present embodiment, the same portions as those in the above embodiments are denoted with the same reference signs and a description thereof is omitted here, and only differences are described.

Figure 33:
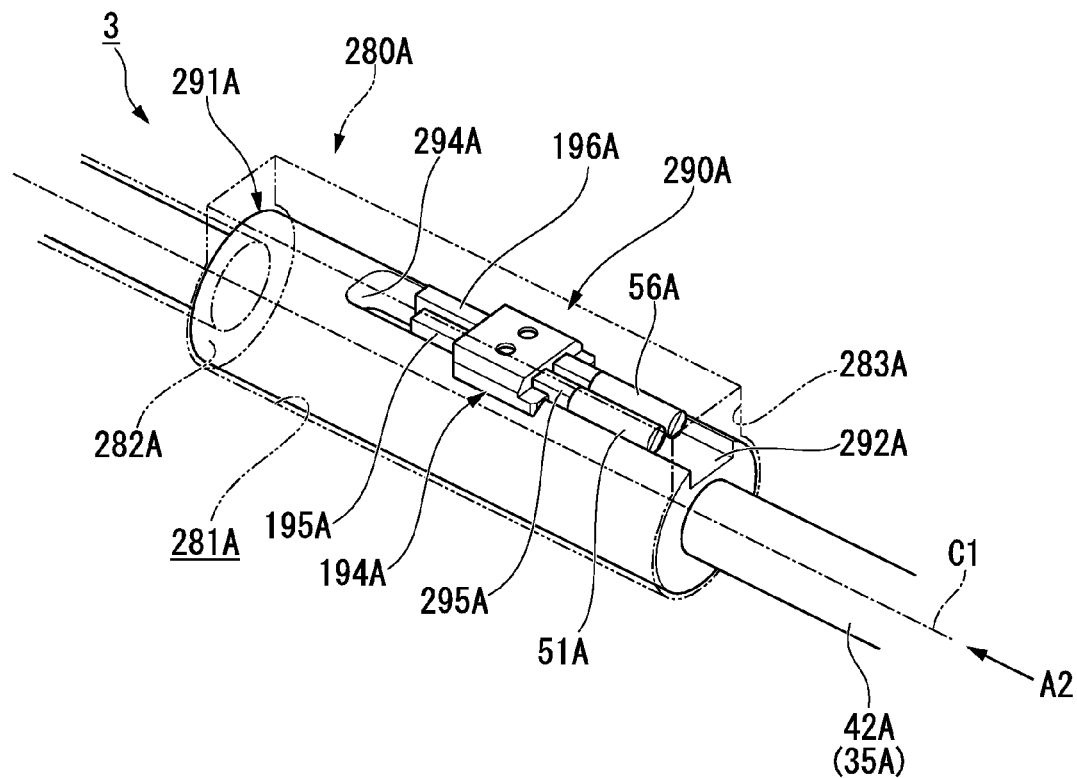
FIG. 33 is a perspective view in which a major part of a manipulator system including a position detection sensor and a manipulator according to a seventh embodiment of the present invention are transmitted.
Figure 34:
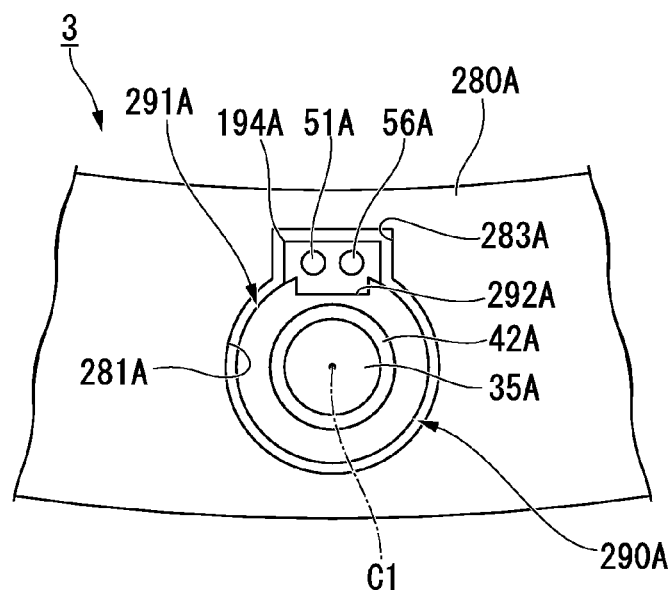
FIG. 34 is a view of FIG. 33 viewing from an arrow direction A2.
Figure 35:
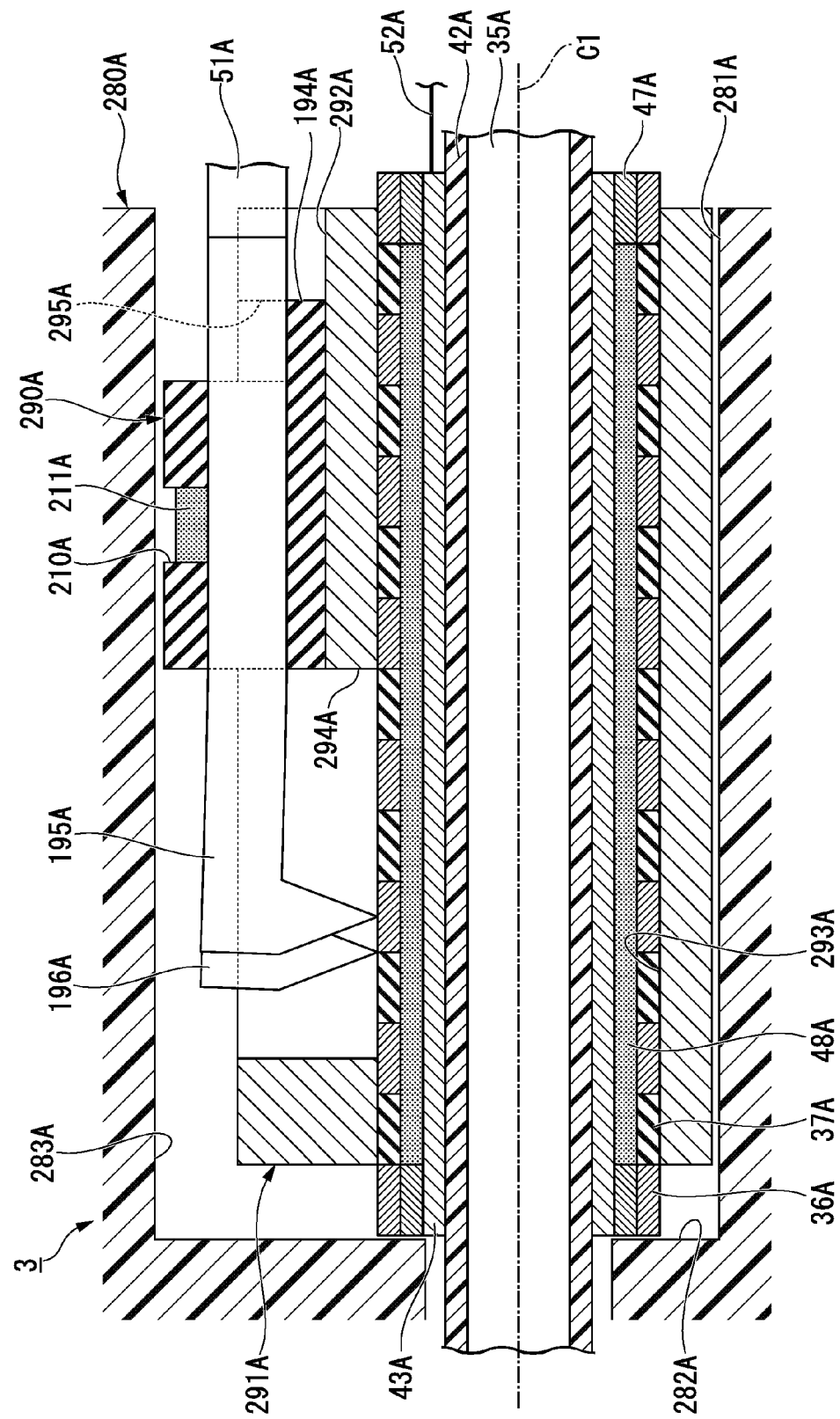
FIG. 35 is a cross-sectional view of a major part of the position detection sensor.

In the present embodiment, in a manipulator system 3, a pair of through holes 281A are formed in an attachment member 280A formed in an annular shape, as illustrated in FIGS. 33 to 35. A position detection sensor 290A according to the present embodiment is attached in each of the pair of through holes 281A. In FIGS. 33 to 35, only one through hole 281A and only one position detection sensor 290A are illustrated.

The through hole 281A is formed in a cylindrical shape. A distal side of the through hole 281A is reduced in diameter to form a step portion 282A in the through hole 281A. A concave portion 283A recessed outward in a radial direction is formed in an inner periphery of a portion on a proximal side of the through hole 281A having a large inner diameter.

The position detection sensor 290A includes a support member 291A formed in a cylindrical shape, in place of the support member 193A of the position detection sensor 184A according to the sixth embodiment.

An outer diameter of the support member 291A is slightly smaller than the inner diameter of the portion on the proximal side of the through hole 281A. A groove 292A extending from a proximal end to a distal end of the support member 291A is formed in an outer periphery of the support member 291A. A communicating hole 294A which communicates with a cylindrical hole 293A of the support member 291A is formed in a distal end portion of the groove 292A. A widened portion 295A is provided in the groove 292A. The widened portion 295A is arranged closer to a proximal side of the groove 292A than the communicating hole 294A, and is formed to be wider than other portions of the groove 292A. It is preferable that the support member 291A is formed of a material having insulation properties such as a resin or ceramics.

The holding member 194A is fixed to the support member 291A with an adhesive or the like in a state in which the holding member 194A is engaged with the widened portion 295A. The holding member 194A is engaged with the widened portion 295A, so that the holding member 194A is prevented from moving in the direction of the axis C1 and rotating around the axis C1 with respect to the support member 291A when the holding member 194A is positioned in the support member 291A prior to fixation with the adhesive.

The wirings 51A and 56A connected to the contact probes 195A and 196A are accommodated in the groove 292A of the support member 291A, and are routed on the proximal side.

A procedure of attaching the position detection sensor 290A to the attachment member 280A is as follows.

The position detection sensor 290A is inserted into the through hole 281A of the attachment member 280A from the proximal end of the through hole 281A. A distal end portion of the manipulation wire 35A is inserted into the through hole 281A, and the holding member 194A of the position detection sensor 290A is engaged with the concave portion 283A of the through hole 281A. Accordingly, the position detection sensor 290A is prevented from rotating about the axis C1 with respect to the through hole 281A.

The position detection sensor 290A is pushed to the distal end so that the distal end portion of the connecting pipe 43A or the support member 291A is brought into contact with the step portion 282A. Accordingly, the position detection sensor 290A is positioned in the direction of the axis C1 with respect to the attachment member 280A. An adhesive or the like (not illustrated) is injected into the through hole 281A to become solidified, so that the support member 291A of the position detection sensor 290A or the like is fixed to the attachment member 280A.

According to the position detection sensor 290A having the above configuration according to the present embodiment, the outer diameter can be reduced. In the manipulator 19A including the position detection sensor 290A, the outer diameter of the bending portion 23A can be reduced. The position detection sensor 290A can be easily positioned with respect to the attachment member 280A.

Figure 36:
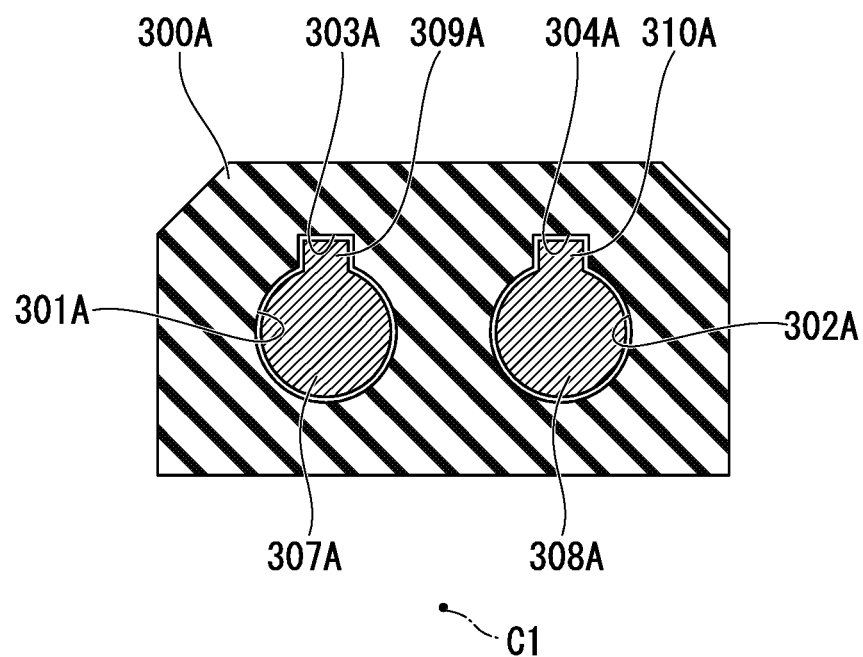
FIG. 36 is a cross-sectional view of a major part of a position detection sensor in a modified example of the position detection sensor according to the seventh embodiment of the present invention.

In the sixth embodiment and the seventh embodiment, the cross-sectional shape of each of the holding holes 208A and 209A of the holding member 194A in a plane orthogonal to the axis C1 is a rectangular shape, and the cross-sectional shape of each of the plate springs 215A and 220A in the plane is a rectangular shape. However, a cross-sectional shape of each of a first holding hole 301A and a second holding hole 302A of a holding member 300A in the plane orthogonal to the axis C1 may be a circular shape, and concave portions 303A and 304A which are key grooves recessed from the inner periphery to the outer side in the radial direction may be formed in the first holding hole 301A and the second holding hole 302A, respectively, as illustrated in FIG. 36.

In this case, a first biasing member 307A and a second biasing member 308A are formed in a cylindrical shape, and convex portions 309A and 310A which are keys projecting from the outer periphery to the outside in the radial direction are formed in the first biasing member 307A and the second biasing member 308A, respectively. Cross-sectional shapes of the first biasing member 307A and the second biasing member 308A are slightly smaller than the cross-sectional shapes of the first holding hole 301A and the second holding hole 302A described above, respectively.

The first biasing member 307A is inserted into the first holding hole 301A of the holding member 300A, and the convex portion 309A of the first biasing member 307A is engaged with the concave portion 303A of the first holding hole 301A. Accordingly, the first biasing member 307A is prevented from rotating about its own longitudinal direction in the first holding hole 301A. The same applies to the second holding hole 302A and the second biasing member 308A.

Figure 37:
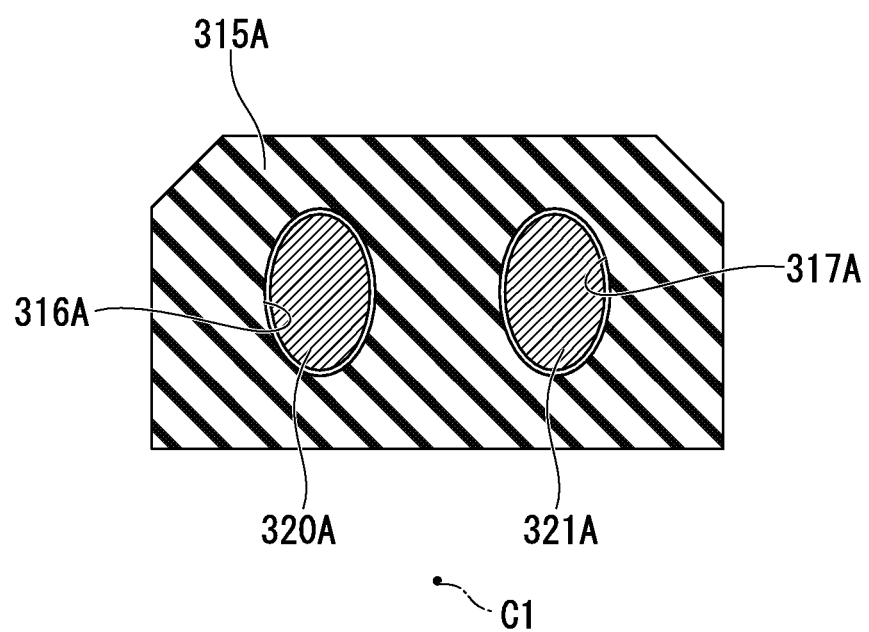
FIG. 37 is a cross-sectional view of a major part of a position detection sensor in a modified example of the position detection sensor according to the seventh embodiment of the present invention.

A cross-sectional shape of each of a first holding hole 316A and a second holding hole 317A of a holding member 315A in the plane orthogonal to the axis C1 may be an elliptical shape, as illustrated in FIG. 37. In this case, cross sections of a first biasing member 320A and a second biasing member 321A are formed in an elliptic pillar shape. The cross-sectional shapes of the first biasing member 320A and the second biasing member 321A are slightly smaller than the cross-sectional shapes of the first holding hole 316A and the second holding hole 317A described above, respectively.

Through this configuration, it is also possible to achieve the same effects as those in the example of the holding member 300A and the biasing members 307A and 308A described above.

Figure 38:
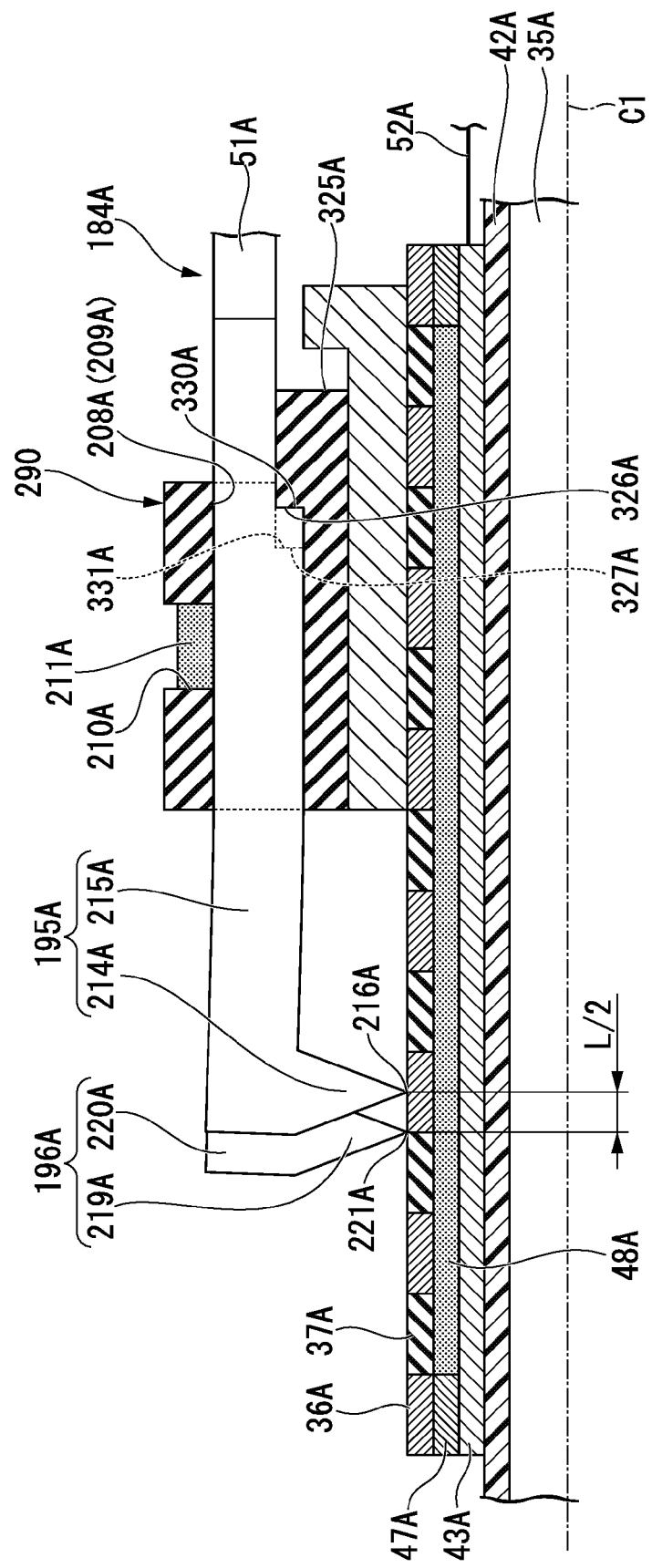
FIG. 38 is a cross-sectional view of a major part of a position detection sensor in a modified example of the position detection sensor according to the seventh embodiment of the present invention.

A step portion 326A may be formed in the first holding hole 208A of a holding member 325A by making a diameter of a proximal end portion of the first holding hole 208A less than that of a distal end portion thereof, as illustrated in FIG. 38. A step portion 327A may be formed in the second holding hole 209A of the holding member 325A by making a diameter of a proximal end portion of the second holding hole 209A less than that of a distal end portion thereof. In this case, a step portion 330A is formed in the first plate spring 215A of the first contact probe 195A by making a diameter of a proximal end portion of the first plate spring 215A less than that of a distal end portion thereof. A step portion 331A is formed in the second plate spring 220A of the second contact probe 196A by making a diameter of a proximal end portion of the second plate spring 220A less than that of a distal end portion thereof.

The step portion 330A of the first plate spring 215A inserted into the first holding hole 208A from a distal end of the first plate spring 215A is engaged with the step portion 326A of the first holding hole 208A, so that the first contact probe 195A is positioned with respect to the holding member 325A in the direction of the axis C1. Similarly, the step portion 331A of the second plate spring 220A inserted into the second holding hole 209A from a distal end of the second plate spring 220A is engaged with the step portion 327A of the second holding hole 209A, so that the second contact probe 196A is positioned with respect to the holding member 325A in the direction of the axis C1. Positions of the step portions 326A and 327A of the holding member 325A and the step portions 330A and 331A of the contact probes 195A and 196A in the direction of the axis C1 are adjusted such that the distal end 221A of the second contact probe 196A is shifted to the distal end by approximately a half of the length L relative to the distal end 216A of the first contact probe 195A when the contact probes 195A and 196A are positioned with respect to the holding member 325A.

Thereafter, the positions of the contact probes 195A and 196A with respect to the holding member 325A may be adjusted while observing the contact probes 195A and 196A through a stereomicroscope or the like, as necessary.

As described above, the contact probes 195A and 196A are fixed to the holding member 325A with the adhesive 211A.

Through this configuration, the distance between the distal ends 216A and 221A of the contact probes 195A and 196A can be easily adjusted.

In the sixth embodiment and the seventh embodiment, the conductive portion and the insulating portion are formed in a ring shape and provided over the entire circumference of the manipulation wire 35A. However, the shapes of the conductive portion and the insulating portion are not limited thereto, and may be, for example, flat shapes as shown in the fifth embodiment. In this case, the conductive portion and the insulating portion are provided so as to cover a portion of an outer surface of the manipulation wire 35A.

The position T9 in which the distal end 221A of the second contact member 219A comes in contact with the outer peripheries of the rings 36A and 37A is shifted to the distal end by a half of the length L relative to the position T8 in which the distal end 216A of the first contact member 214A comes in contact. However, the position T9 in which the distal end 221A of the second contact member 219A comes in contact may be shifted to the proximal end by a half of the length L relative to the position T8 in which the distal end 216A of the first contact member 214A comes in contact. When N is assumed to be a natural number, a distance by which the position T9 and the position T8 are shifted in the direction of the axis C1 may be equal to a value obtained using an expression of L(N−1/2). That is, 3L/2, 5L/2, . . . , or the like, as well as L/2 may be used.

A fixing portion is the adhesive 211A. However, the fixing portion is not limited thereto, and screws or the like may be appropriately used as the fixing portion when the outer diameter of the position detection sensor is relatively large.

The connecting pipe 43A may not be included in the position detection sensor. A lead connected to each conductive ring 36A is connected to the first detector 83 or the like, so that the position of the manipulation wire 35A in the direction of the axis C1 with respect to the support member 193A can be detected. When the position detection sensor is used in a place with less electromagnetic noise, the covering material 42A may not be included in the position detection sensor.

In the sixth embodiment and the seventh embodiment, while the distal ends 216A and 221A of the contact member and the outer peripheries of the conductive ring 36A and the insulating ring 37A have been described as being able to be brought into contact in a point form, the configurations of the distal ends 216A and 221A, the conductive ring 36A, and the insulating ring 37A are not limited thereto. They may be configured to be brought into contact in a surface shape.

The position detection sensor according to each embodiment described above may be appropriately used for devices such as a medical treatment tool or an experimental device manipulated using a wire, as well as the manipulator.

While the preferred embodiments of the present invention have been described above, the present invention is not limited to the embodiments. Additions, omissions, substitutions, and other modifications can be made to the present invention without departing from the scope of the present invention. The present invention is not limited to the foregoing description, and is only limited by the scope of the appended claims.

What is claimed is:

1. A position detection sensor comprising:
a linear member;
a conductive portion and an insulating portion provided in an outer periphery of the linear member, the conductive portion and the insulating portion being arranged side by side in a direction of an axis of the linear member;
a support member having insulating properties, the support member being provided so as to be capable of being relatively advanced or retracted in the direction of the axis with respect to the conductive portion and the insulating portion;
a conductive contact member attached to the support member, the contact member being configured such that a distal end of the contact member comes in contact with outer surfaces of the conductive portion and the insulating portion by a biasing force toward the outer surfaces of the conductive portion and the insulating portion;
a first biasing member configured to generate the biasing force;
a second biasing member configured to generate the biasing force,
a holding member configured to hold the first biasing member and the second biasing member; and
a fixing portion configured to fix the first biasing member and the second biasing member to the holding member, wherein
the first biasing member and the second biasing member are attached to the support member together with the holding member,
the contact member includes a first contact member attached to the first biasing member and a second contact member attached to the second biasing member,
the conductive portion is provided in plural numbers, and the insulating portion is provided in plural numbers,
each of the plurality of conductive portions and each of the plurality of insulating portions are alternately arranged in the direction of the axis, and
the holding member holds the first biasing member and the second biasing member such that a distance in the direction of the axis between a position in which the second contact member comes in contact with the plurality of conductive portions or the plurality of insulating portions and a position in which the first contact member comes in contact with the plurality of conductive portions or the plurality of insulating portions becomes a predetermined distance.

2. The position detection sensor according to claim 1, wherein the conductive portion and the insulating portion are provided over an entire circumference of the linear member.

3. The position detection sensor according to claim 2, further comprising
a second conductive portion arranged side by side in the direction of the axis with the conductive portion and the insulating portion, a length of the second conductive portion in the direction of the axis being set to be equal to or more than a length of the conductive portion, wherein
the contact member includes a first contact member, a second contact member, a third contact member, and a fourth contact member,
a position in which the second contact member comes in contact with the conductive portion, the insulating portion, or the second conductive portion is shifted to a proximal end of the linear member by a half of the length of the conductive portion in the direction of the axis relative to a position in which the first contact member comes in contact with the conductive portion, the insulating portion, or the second conductive portion,
a position in which the third contact member comes in contact with the conductive portion, the insulating portion, or the second conductive portion is shifted to the proximal end of the linear member by a half of the length of the conductive portion in the direction of the axis relative to the position in which the second contact member comes in contact with the conductive portion, the insulating portion, or the second conductive portion, and
a position in which the fourth contact member comes in contact with the conductive portion, the insulating portion, or the second conductive portion is shifted to the proximal end of the linear member by a half of the length of the conductive portion in the direction of the axis relative to the position in which the third contact member comes in contact with the conductive portion, the insulating portion, or the second conductive portion.

4. The position detection sensor according to claim 1, wherein
  a first holding hole extending in the direction of the axis is formed in the holding member, wherein the first biasing member is capable of being inserted into the first holding hole, and
  a rotation prevention portion configured to prevent the first biasing member from rotating around a longitudinal direction of the first biasing member in the first holding hole is provided in the first holding hole.

5. The position detection sensor according to claim 1, wherein
  a length of each of the plurality of conductive portions in the direction of the axis and a length of each of the plurality of insulating portions in the direction of the axis are equal to each other, and
  when the length of each of the plurality of conductive portions in the direction of the axis is L and N is a natural number, the predetermined distance is equal to a value obtained using an expression of L(N−1/2).

6. A manipulator comprising:
  the position detection sensor according to claim 1; and
  a pivoting member pivotably supported by the support member, wherein
  a distal end portion of the linear member is attached to the pivoting member.

7. A position detection sensor comprising:
  a linear member;
  a conductive portion and an insulating portion provided in an outer periphery of the linear member, the conductive portion and the insulating portion being arranged side by side in a direction of an axis of the linear member;
  a support member having insulating properties, the support member being provided so as to be capable of being relatively advanced or retracted in the direction of the axis with respect to the conductive portion and the insulating portion;
  a conductive contact member attached to the support member, the contact member being configured such that a distal end of the contact member comes in contact with outer surfaces of the conductive portion and the insulating portion by a biasing force toward the outer surfaces of the conductive portion and the insulating portion; and
  a conductive tubular member provided between the conductive portion and the insulating portion, and the linear member, the tubular member being electrically connected to the conductive portion, wherein
  the conductive portion is provided in plural numbers,
  the insulating portion is arranged between the plurality of conductive portions adjacent in the direction of the axis, and
  a length of each of the plurality of conductive portions in the direction of the axis and a length of the insulating portion in the direction of the axis are set to be substantially equal to each other.

8. The position detection sensor according to claim 7, further comprising
  an insulating covering material which covers the outer periphery of the linear member, wherein
  the contact member includes a first contact member and a second contact member, and
  a position in which the second contact member comes in contact with the plurality of conductive portions or the insulating portion is shifted in the direction of the axis by a half of the length of each of the plurality of conductive portions in the direction of the axis relative to a position in which the first contact member comes in contact with the plurality of conductive portions or the insulating portion.

9. The position detection sensor according to claim 7, wherein
  the contact member includes a first contact member and a second contact member,
  the linear member has conductivity,
  the linear member is electrically connected to the tubular member,
  a position in which the second contact member comes in contact with the plurality of conductive portions or the insulating portion is shifted in the direction of the axis by a half of the length of each of the plurality of conductive portions in the direction of the axis relative to a position in which the first contact member comes in contact with the plurality of conductive portions or the insulating portion.

10. The position detection sensor according to claim 7, wherein
  the contact member includes a first contact member formed in a spherical shape and a second contact member formed in a spherical shape, and
  a position in which the second contact member comes in contact with the plurality of conductive portions or the insulating portion is shifted in the direction of the axis by a half of the length of each of the plurality of conductive portions in the direction of the axis relative to a position in which the first contact member comes in contact with the plurality of conductive portions or the insulating portion.

11. The position detection sensor according to claim 7, further comprising
  a receiving member including a concave portion opened toward the axis of the linear member, the receiving member being formed of a conductive material, wherein
  the receiving member is configured to rotatably support the contact member in the concave portion.

12. A manipulator comprising:
  the position detection sensor according to claim 7; and
  a pivoting member pivotably supported by the support member, wherein
  a distal end portion of the linear member is attached to the pivoting member.

13. The position detection sensor according to claim 7, wherein the conductive portion and the insulating portion are provided over an entire circumference of the linear member.

14. The position detection sensor according to claim 13, further comprising
  a second conductive portion arranged side by side in the direction of the axis with the conductive portion and the insulating portion, a length of the second conductive portion in the direction of the axis being set to be equal to or more than a length of the conductive portion, wherein
  the contact member includes a first contact member, a second contact member, a third contact member, and a fourth contact member,
  a position in which the second contact member comes in contact with the conductive portion, the insulating portion, or the second conductive portion is shifted to a proximal end of the linear member by a half of the length of the conductive portion in the direction of the axis relative to a position in which the first contact member comes in contact with the conductive portion, the insulating portion, or the second conductive portion, a position in which the third contact member comes in contact with the conductive portion, the insulating portion, or the second conductive portion is shifted to the proximal end of the linear member by a half of the length of the conductive portion in the direction of the axis relative to the position in which the second contact member comes in contact with the conductive portion, the insulating portion, or the second conductive portion, and a position in which the fourth contact member comes in contact with the conductive portion, the insulating portion, or the second conductive portion is shifted to the proximal end of the linear member by a half of the length of the conductive portion in the direction of the axis relative to the position in which the third contact member comes in contact with the conductive portion, the insulating portion, or the second conductive portion.

15. A position detection sensor comprising:

a linear member;

a conductive portion and an insulating portion provided in an outer periphery of the linear member, the conductive portion and the insulating portion being arranged side by side in a direction of an axis of the linear member;

a support member having insulating properties, the support member being provided so as to be capable of being relatively advanced or retracted in the direction of the axis with respect to the conductive portion and the insulating portion;

a conductive contact member attached to the support member, the contact member being configured such that a distal end of the contact member comes in contact with outer surfaces of the conductive portion and the insulating portion by a biasing force toward the outer surfaces of the conductive portion and the insulating portion; and a holding member provided in the outer periphery of the linear member, the holding member including a holding surface parallel to the axis of the linear member in an outer surface of the holding member, wherein the conductive portion and the insulating portion are arranged on the holding surface, and the support member is configured to be capable of being advanced or retracted in the direction of the axis with respect to the conductive portion and the insulating portion, and is configured to prevent the linear member from rotating in a circumferential direction with respect to the conductive portion and the insulating portion.

16. A manipulator comprising:

the position detection sensor according to claim 15; and a pivoting member pivotably supported by the support member, wherein a distal end portion of the linear member is attached to the pivoting member.

17. The position detection sensor according to claim 15, wherein the conductive portion and the insulating portion are provided over an entire circumference of the linear member.

18. The position detection sensor according to claim 17, further comprising a second conductive portion arranged side by side in the direction of the axis with the conductive portion and the insulating portion, a length of the second conductive portion in the direction of the axis being set to be equal to or more than a length of the conductive portion, wherein the contact member includes a first contact member, a second contact member, a third contact member, and a fourth contact member, a position in which the second contact member comes in contact with the conductive portion, the insulating portion, or the second conductive portion is shifted to a proximal end of the linear member by a half of the length of the conductive portion in the direction of the axis relative to a position in which the first contact member comes in contact with the conductive portion, the insulating portion, or the second conductive portion, a position in which the third contact member comes in contact with the conductive portion, the insulating portion, or the second conductive portion is shifted to the proximal end of the linear member by a half of the length of the conductive portion in the direction of the axis relative to the position in which the second contact member comes in contact with the conductive portion, the insulating portion, or the second conductive portion, and a position in which the fourth contact member comes in contact with the conductive portion, the insulating portion, or the second conductive portion is shifted to the proximal end of the linear member by a half of the length of the conductive portion in the direction of the axis relative to the position in which the third contact member comes in contact with the conductive portion, the insulating portion, or the second conductive portion.

* * * * *